United States Patent

Ando et al.

[11] Patent Number: 6,048,986
[45] Date of Patent: Apr. 11, 2000

[54] METHOD FOR PREPARING AROMATIC COMPOUNDS

[75] Inventors: Shinji Ando, Tokyo; Toru Matsuura, Yokohama; Shigekuni Sasaki, Iruma; Fumio Yamamoto, Katsuta, all of Japan

[73] Assignee: Nippon Telegraph and Telephone Corp., Tokyo, Japan

[21] Appl. No.: 09/098,605

[22] Filed: Jun. 17, 1998

Related U.S. Application Data

[62] Division of application No. 09/020,573, Jan. 28, 1998, Pat. No. 5,849,934, which is a division of application No. 08/718,208, Sep. 20, 1996, Pat. No. 5,750,731, which is a continuation of application No. 08/451,465, May 26, 1995, abandoned, which is a division of application No. 08/140, 482, Oct. 25, 1993, Pat. No. 5,449,741, which is a continuation-in-part of application No. 08/054,973, Apr. 30, 1993, abandoned, which is a division of application No. 07/765, 672, Sep. 26, 1991, Pat. No. 5,233,018.

[30] Foreign Application Priority Data

| Sep. 28, 1990 | [JP] | Japan | 2-56843 |
| Apr. 12, 1991 | [JP] | Japan | 3-106552 |
| Apr. 12, 1991 | [JP] | Japan | 3-106554 |
| Apr. 21, 1991 | [JP] | Japan | 3-106557 |

[51] Int. Cl.[7] ............................................. C07D 493/04
[52] U.S. Cl. ........................ 549/239; 558/420; 562/484
[58] Field of Search ............................ 549/239; 558/420; 562/484

[56] References Cited

U.S. PATENT DOCUMENTS

| 3,356,648 | 12/1967 | Rogers | 260/47 |
| 3,959,350 | 5/1976 | Rogers | 260/47 |
| 4,760,126 | 7/1988 | Numata et al. | 528/353 |
| 5,009,679 | 4/1991 | Angus et al. | 55/16 |
| 5,061,784 | 10/1991 | Mueller et al. | 528/353 |
| 5,177,179 | 1/1993 | Auman et al. | 528/353 |
| 5,260,408 | 11/1993 | Auman et al. | 528/353 |

FOREIGN PATENT DOCUMENTS

| 0317944 | 5/1989 | European Pat. Off. . |
| 0397153 | 11/1990 | European Pat. Off. . |
| 0410793 | 1/1991 | European Pat. Off. . |
| 59-189122 | 10/1984 | Japan . |
| 62-127826 | 6/1987 | Japan . |
| 1-1185627 | 5/1989 | Japan . |
| 2-15084 | 1/1990 | Japan . |
| 3-72528 | 3/1991 | Japan . |
| 4328133 | 11/1992 | Japan . |
| 4328732 | 11/1992 | Japan . |
| 4328891 | 11/1992 | Japan . |
| 5113501 | 5/1993 | Japan . |
| 6003713 | 1/1994 | Japan . |
| 6157501 | 6/1994 | Japan . |

OTHER PUBLICATIONS

"Plastic optical fibers for near–infrared transmission", Kaino, Applied Phys. Lett. 48 (12) Mar. 24, 1986, pp. 757–758.

"Optical Waveguiding in Polyimide", Franke et al. SPIE, vol. 651, Integrated Optical Circuit Engineering, III, pp. 102–107, 1986.

"Optical waveguide circuits for printed wire–board interconnections", Sullivan, SPIE, vol. 994, Optoelectronic Materials, Devices, . . . II, pp. 92–100, 1988.

"Evaluation of Colorless Polyimide Film for Thermal Control Coating Applications", St. Clair et al., SAMPE Journal, Jul./Aug., pp. 28–33, 1985.

"Evaluating polyimides as lightguide materials", Rueter et al., Applied Optics, vol. 27, No. 21, pp. 4565–4571 (1988).

"Polyimides Based on 3.6–Diphenoxpryomellitic Dianhydride", Brandelik et al., ACS Polymer Preprint, 28 (1), pp. 88–89, 1987.

"Perfluoroalkylene–Linked Aromatic Polyimides", Critchley et al., J. Polym. Sci., A–1, 10, pp. 1789–1807, 1972.

"Syntheses of Fluoroorganic Compounds", ed. Knunyants et al., Springer–Verlag, Berlin, pp. 193–232, 1985.

L. Kobrina et al., Zh. Obshch, Khim, 38, 514, 1968.

"Aromatic Nucleophylic Substitution XVII. The Derivatives of Polyfluoro–rinated Diphenylsulphide and Diphenylsulphone", G. Furin et al. SSSR, Ser. Khim., 1976.

(List continued on next page.)

*Primary Examiner*—Richard L. Raymond
*Attorney, Agent, or Firm*—Venable; Robert J. Frank; Ashley J. Wells

[57] ABSTRACT

A method for preparing aromatic compounds including 1,4-difluoropyromellitic dianhydride represented by formula (12):

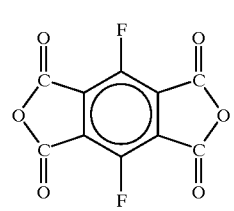

(12)

and 1,4-difluoropyromellitic acid represented by formula (15):

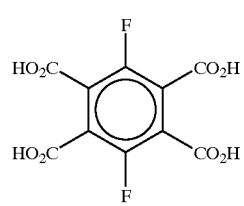

(15)

by dehydrating or hydrolyzing and dehydrating precursors.

3 Claims, 2 Drawing Sheets

OTHER PUBLICATIONS

"Trifluoromethylation of Aromatic Compounds", Kobayashi et al., Tetrahed–ron Letters, 47, pp. 4095–4096, 1969.

Polymer Preprints, Japan, vol. 40, No. 3, pp. 826–830, 1991, Items III–11–07 to 11–11, May 10, 1991.

Polymer Preprints, Japan, vol. 39, No. 3, pp. 790–794, 1990, Items III–11–01 to 11–05.

Polymer Preprints, Japan, vol. 38, No. 3, pp. 433–436 and 798, 1989, Items 13H–03 to 06 and 14Pb14.

"Synthesis and Properties of Novel Fluorinated Polyimides", Preprint of First Pacific Polymer Conference, Dec. 12–15, 1989, Maui, Hawaii.

Mochizuki, H., et al., *Chemical Abstracts*, vol. 112, Abstract No. 112:88030 1990.

J. Duncan et al., "Effect of Structural Rearrangement on the Mollusi–cidal Activity of Certain Fluorinated Aromatic Compounds", *Chem. Abst.*, vol. 73: 76068f, 1970, pp. 820–825.

Ando et al., Magn. *Reson. Chem.*, 1995, 33 (8), 639–645.

Okumura et al., *Chem. Abst.*, 120: 298457, 1994.

Kaieda et al., *Chem. Abst.*, 121: 35030, 1994.

Ando et al., *Polym. Mater Sci. Eng.*, 1992, 66, 200–201.

METHOD FOR PREPARING AROMATIC COMPOUNDS

This is a division of application Ser. No. 09/020,573 filed Jan. 28, 1998, now U.S. Pat. No. 5,849,934,; which is a division of application Ser. No. 08/718,208 filed Sep. 20, 1996, now U.S. Pat. No. 5,750,731,; which is a continuation of application Ser. No. 08/451,465 filed May 26, 1995, now abandoned,; which is a division of application Ser. No. 08/140,982 filed Oct. 25, 1993 now U.S. Pat. No. 5,449,741; which is a continuation-in-part application of Ser. No. 08/054,973 filed Apr. 30, 1993, now abandoned; which is a division of application Ser. No. 07/765,672 filed Sep. 26, 1991 now U.S. Pat. No. 5,233,018.

BACKGROUND OF THE INVENTION

1. Field of the Invention

The present invention relates to a fluorinated polyimide optical material and more particularly to a fluorinated polyimide optical material having a low transmission loss in near-infrared region which can be used as an optical material for light guiding in opto-electronic integrated circuits or implemented optical-electrical mixed wiring boards. Furthermore, the present invention relates to a fluorinated polyimide which can be used as a major component of such an optical material, to a fluorinated poly(amic acid) which is an intermediate or precursor for a fluorinated polyimide, and to fluorinated tetracarboxylic acids or their dianhydride, which are starting compounds for the preparation of the fluorinated poly(amic acid), as well as to methods for preparing the fluorinated polyimide, fluorinated poly(amic acid), and starting compounds, respectively.

2. Description of the Related Arts

Plastic materials are generally lighter in weight than inorganic materials and are featured by a higher impact strength, a higher processability, easier handling and the like and they have heretofore been used widely for various optical purposes such as optical fibers or lenses, substrates for optical discs. When plastics are to be used as media for transmitting near-infrared lights for optical transmission such as optical waveguides for opto-electronic integrated circuits (OEIC), optical electronic mixed implemented wiring boards, a problem arises that plastics have high optical losses as compared with inorganic materials. Causes of light transmission loss in plastics are roughly classified into two factors, i.e., scattering and absorption. According as the wavelengths of lights used in light transmission are shifted toward longer wavelength regions (from 0.85 $\mu$m to 1.0 $\mu$m~1.7 $\mu$m) the latter cause, i.e., optical loss ascribable to high harmonic absorption of infrared vibration which is inherent to the molecular structure of the material will become dominant, and thus it is feared that use of plastics in light transmission applications would be difficult. In particular, poly(methyl methacrylate) (PMMA) and polystyrene (PS) which have been widely used as an optical material for a visible light region have two or more types of carbon-to-hydrogen bonds (C—H bonds) in the molecular chain and hence there are a plurality of broad, strong absorption peaks in near-infrared absorption spectra. To decrease the intensity of harmonics absorption due to C—H bonds by shifting it toward longer wavelength region, it has been indicated that substitution of hydrogens in the molecule with deuterium (D) or fluorine (F) is effective, and there have already been made fundamental studies on PMMA and PS materials of which hydrogens were substituted with deuterium or fluorine (cf., e.g., Toshikuni Kaino, Appl. Phys. Lett., 48, No. 12, p. 757 (1986)) However, these plastic optical materials have insufficient soldering resistances (260° C.) required for the fabrication of OEIC on a silicone substrate, which necessitates various devices about fabrication steps when they are applied to OEIC and the like.

On the other hand, polyimides generally have a thermal decomposition initiation temperature of 400° C. or higher and are known as one of those having the highest thermal resistance among the plastics, and their application to optical materials has recently come to be studied. (cf. e.g., H. Franke, J. D. Crow, SPIE, Vol. 651, Integrated Optical Circuit Engineering III, pp. 102–107 (1986); and C. T. Sullivan, SPIE, Vol. 994, p. 92 (1988)).

Further, a fluorine-containing polyimide coating material comprising a polyimide having a hexafluoroisopropylidene group has been studied for its feasibility as a thermal resistant coating material having an improved clarity (Anne K. St. Clair and Wayne S. Slemp, SAMPE Journal, July/August, pp. 28–33 (1985)). On the other hand, with view to decreasing optical losses, there have been proposed optical waveguides comprising a fluorine-containing polyimide having a hexafluoroisopropylidene group in its main chain (cf. Rainer Reuter, Hilmar Franke, and Claudius Feger, Applied Optics, Vol. 27, No. 21, pp. 4565–4571 (1988)).

However, as far as is known, all the polyimides including fluorine-containing polyimides thus far proposed or available have C—H bonds in phenyl groups in the polymer chain and therefore their absorption spectra in near-infrared region contain peaks which can be assigned to harmonics due to the stretching vibration of C—H bonds or to a combination of harmonics due to the stretching vibration and deformation vibration of C—H bonds. As a result, low optical loss over the entire range of optical transmission wavelength region (1.0 to 1.7 $\mu$m) has remained to be achieved.

Accordingly, theoretically perdeuteration or perfluorination of polyimide will reduce optical losses in optical transmission wavelength region However, as far as is known there has been no report on the synthesis of perdeuterated or perfluorinated polyimides. Perdeuteration would seem insufficient for decreasing absorption peaks over the entire optical transmission wavelength region because third harmonics due to C—D bond appear near a wavelength of 1.5 $\mu$m.

In summary, no plastics optical material has been known that fulfils both requirements of a high optical transmission over the entire optical wavelength region and a high thermal resistance simultaneously.

SUMMARY OF THE INVENTION

The present inventors have examined various conventional polyimides and polyimide optical materials to measure their absorption spectra in infrared and near-infrared regions and calculated their optical losses in near-infrared region, and studies causes for such losses intensively. As a result, it has revealed that optical losses in the near-infrared region are ascribable mainly to harmonics absorption due to stretching vibration of C—H bonds in an alkyl group, a phenyl group or the like, and to absorption due to a combination of a harmonics of stretching vibration and a deformation vibration of C—H bonds.

Therefore, an object of the present invention is to provide a plastics optical material having a thermal resistance enough to fabricate opto-electronic integrated circuits and a decreased optical loss in a near-infrared region, particularly in an optical communication wavelength region (1.0 to 1.7 $\mu$m).

Another object of the present invention is to provide a perfluorinated polyimide and a method for preparing the same.

Still another object of the present invention is to provide a perfluorinated poly(amic acid), which is a precursor for preparing a perfluorinated polyimide, and a method for preparing the same.

Yet another object of the present invention is to provide perfluorinated tetracarboxylic acids or their dianhydrides and perfluorinated diamines (i.e., diamines whose chemical bonds between carbon atoms and monovalent elements being exclusively carbon-to-fluorine bonds), which are starting compounds for preparing a perfluorinated poly(amic acid) or polyimide, and a method for preparing them.

In a first aspect of the present invention, a perfluorinated polyimide comprises a repeating unit represented by general formula (1):

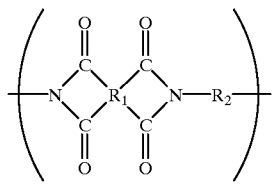
(1)

wherein $R_1$ is a tetravalent organic group; and $R_2$ is a divalent organic group, provided that chemical bonds between carbon atoms and monovalent elements contained in $R_1$ and $R_2$ are exclusively carbon-to-fluorine bonds.

In a second aspect of the present invention, a perfluorinated poly(amic acid) comprises a repeating unit represented by general formula (6):

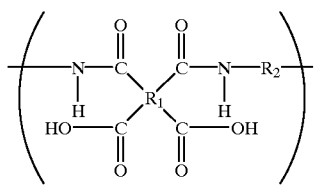
(6)

wherein $R_1$ is a tetravalent organic group; and $R_2$ is a divalent organic group, provided that chemical bonds between carbon atoms and monovalent elements contained in $R_1$ and $R_2$ are exclusively carbon-to-fluorine bonds.

In a third aspect of the present invention, a perfluorinated aromatic compound is represented by general formula (7):

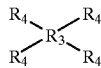
(7)

wherein $R_3$ is a tetravalent perfluorinated aromatic group represented by formula (8) or (9):

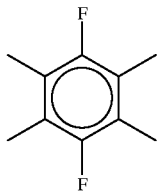
(8)

or

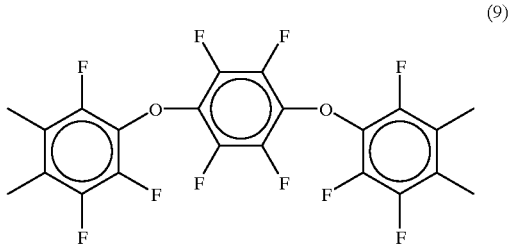
(9)

and four $(R_4)$s are same, each being a carboxyl group or a cyano group, or two adjacent $(R_4)$s combine to form a divalent group represented by formula (10):

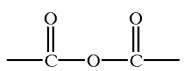
(10)

provided that when $R_4$ is a cyano group, $R_3$ denotes the tetravelent perfluorinated aromatic group represented by formula (9).

In a fourth aspect of the present invention, there is provided 1,4-bis(3,4-dicarboxytrifluorophenoxy) tetrafluorobenzene dianhydride represented by formula (11):

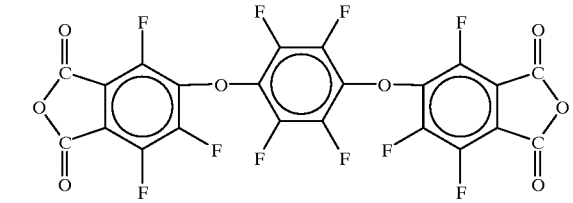
(11)

In a fifth aspect of the present invention, there is provided 1,4-difluoropyromellitic dianhydride represented by formula (12):

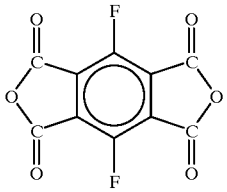
(12)

In a sixth aspect of the present invention, there is provieded 1,4-bis(3,4-dicarboxytrifluorophenoxy) tetrafluorobenzene represented by formula (13):

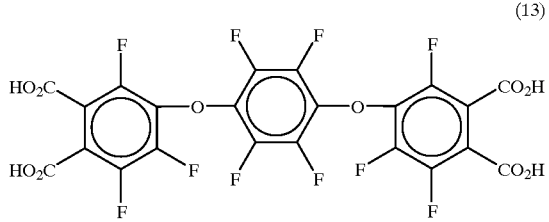

(13)

In a seventh aspect of the present invention, there is provided 1,4-bis(3,4-dicyanotrifluorophenoxy) tetrafluorobenzene represented by formula (14):

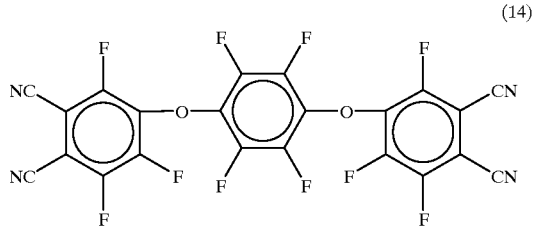

(14)

In an eighth aspect of the present invention, there is provided 1,4-difluoropyromellitic acid represented by formula (15):

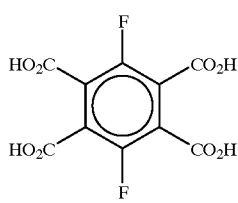

(15)

In a ninth aspect of the present invention, a method for preparing a perfluorinated polyimide having a repeating unit represented by general formula (1):

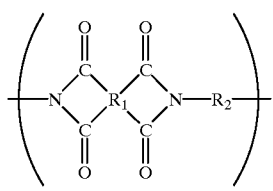

(1)

wherein $R_1$ is a tetravalent organic group; and $R_2$ is a divalent organic group, provided that chemical bonds between carbon atoms and monovalent elements contained in $R_1$ and $R_2$ are exclusively carbon-to-fluorine bonds, comprises the step of:

cyclizing a poly(amic acid) having a repeating unit represented by general formula (6):

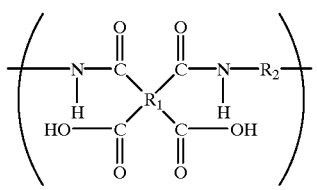

(6)

wherein $R_1$ and $R_2$ have the same meanings as defined above.

In a tenth aspect of the present invention, a method for preparing a perfluorinated poly(amic acid) having a repeating unit represented by general formula (6):

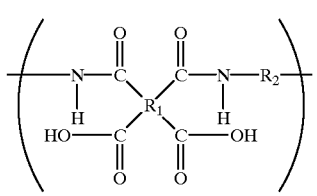

(6)

wherein $R_1$ is a tetravalent organic group; and $R_2$ is a divalent organic group, provided that chemical bonds between carbon atoms and monovalent elements contained in $R_1$ and $R_2$ are exclusively carbon-to-fluorine bonds, comprises the step of:

reacting a tetracarboxylic dianhydride represented by general formula (16):

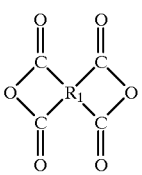

(16)

wherein $R_1$ has the same meaning as defined above, or its corresponding free tetracarboxylic acid or reactive derivative thereof, with a diamine represented by general formula (17):

$$H_2N—R_2—NH_2 \quad (17)$$

wherein $R_2$ has the same meaning as defined above.

In an eleventh aspect of the present invention, a method for preparing 1,4-bis(3,4-dicarboxytrifluorophenoxy) tetrafluorobenzene dianhydride represented by formula (11):

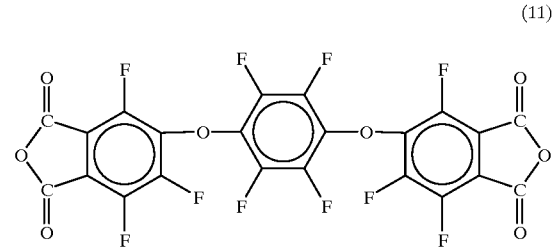

(11)

comprises the step of:

dehydrating 1,4-bis(3,4-dicarboxytrifluorophenoxy) tetrafluorobenzene represented by formula (13):

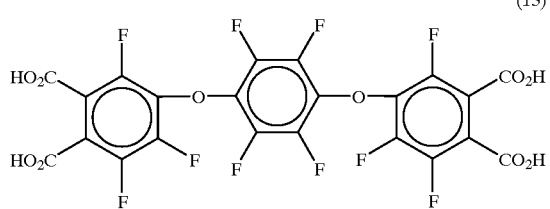
(13)

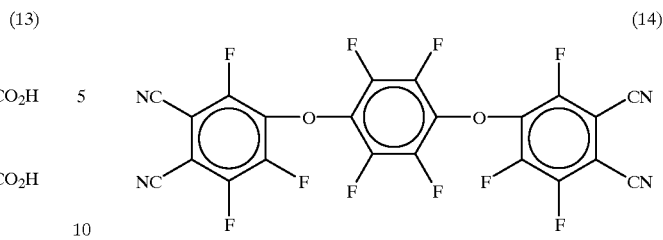
(14)

In a twelfth aspect of the present invention, a method for preparing 1,4-bis(3,4-dicarboxytrifluorophenoxy)tetrafluorobenzene dianhydride represented by formula (11):

In a fourteenth aspect of the present invention, a method for preparing 1,4-bis(3,4-dicyanotrifluorophenoxy)tetrafluorobenzene represented by formula (14):

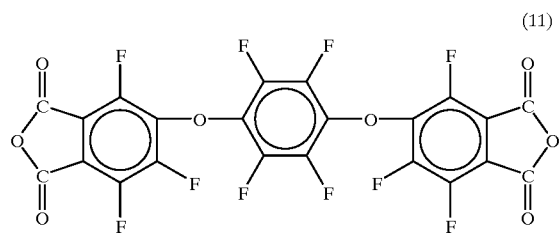
(11)

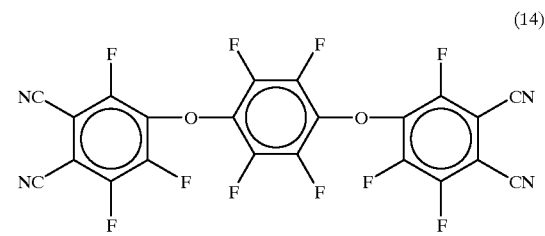
(14)

comprises the step of:

hydrolyzing and dehydrating 1,4-bis(3,4-dicyanotrifluorophenoxy)tetrafluorobenzene represented by formula (14):

comprises the step of:

reacting tetrafluorophthalonitrile with tetrafluorohydroquinone in the presence of a base.

In a fifteenth aspect of the present invention, a method for preparing 1,4-bis(3,4-dicyanotrifluorophenoxy)tetrafluorobenzene represented by formula (14):

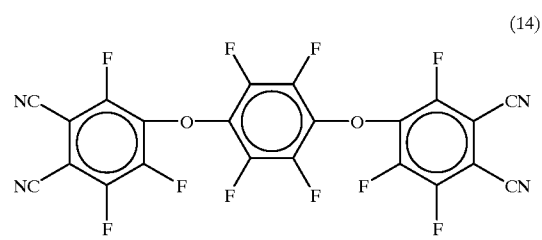
(14)

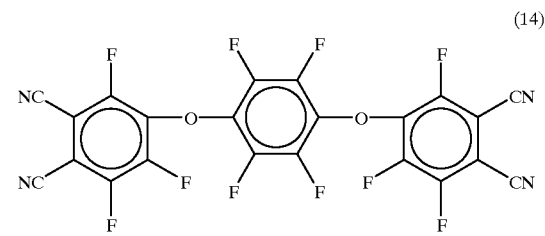
(14)

in sulfuric acid.

In a thirteenth aspect of the present invention, a method for preparing 1,4-bis(3,4-dicarboxytrifluorophenoxy)tetrafluorobenzene represented by formula (13):

comprises the step of:

reacting tetrafluorophthalonitrile with a metal salt of tetrafluorohydroquinone.

In a sixteenth aspect of the present invention, a method for preparing 1,4-difluoropyromellitic dianhydride represented by formula (12):

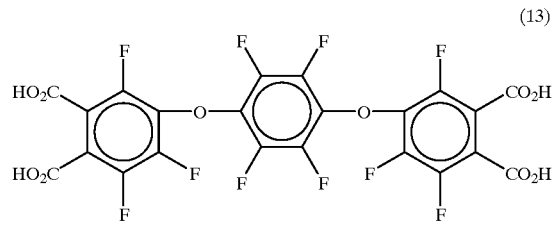
(13)

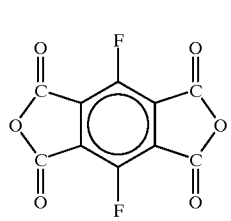
(12)

comprises the step of:

hydrolyzing 1,4-bis(3,4-dicyanotrifluorophenoxy)tetrafluorobenzene represented by formula (14):

comprises the step of:

dehydrating 1,4-difluoropyromellitic acid represented by formula (15):

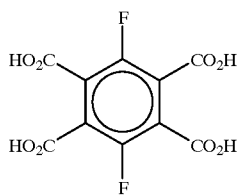
(15)

In an seventeenth aspect of the present invention, a method for preparing 1,4-difluoropyromellitic dianhydride represented by formula (12):

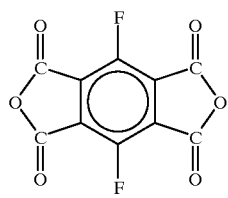
(12)

comprises the step of:

hydrolyzing and dehydrating 1,4-difluorotetracyanobenzene represented by formula (18):

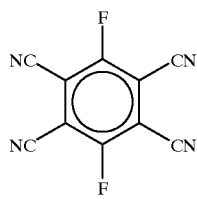
(18)

in sulfuric acid.

In an eighteenth aspect of the present invention, a method for preparing 1,4-difluoropyromellitic acid represented by formula (15):

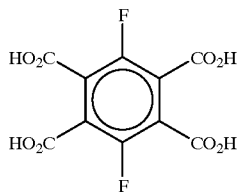
(15)

comprises the step of:

hydrolyzing 1,4-difluorotetracyanobenzene represented by formula (18):

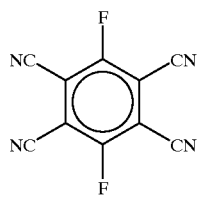
(18)

In a first, second, eighth, ninth and tenth aspects of the present invention, the $R_1$ may be a tetravalent group represented by formula (2):

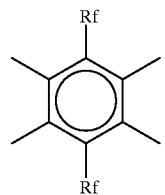
(2)

wherein Rf is a fluorine atom, a perfluoroalkyl group, a perfluoroaryl group, a perfluoroalkoxy group, or a perfluorophenoxy group The $R_1$ may also be a tetravalent group represented by formula (3):

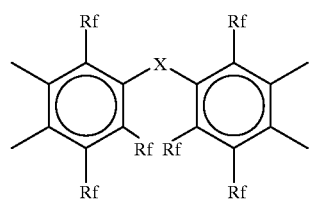
(3)

wherein Rf is a fluorine atom, a perfluoroalkyl group, a perfluoroaryl group, a perfluoroalkoxy group, or a perfluorophenoxy group; X is a simple chemical bond or one member selected from the group consisting of —O—, —CO—, —SO$_2$—, —S—, —Rf'—, —(ORf')$_n$—, —(Rf'O)$_n$—, and —(ORf'O)$_n$— where Rf' is a perfluoroalkylene group, or a perfluoroarylene group, and n is an integer of 1 to 10; or X and two (Rf)s adjacent thereto are combined and form, together with carbon atoms to which they are connected, a saturated or unsaturated, 5- or 6-membered ring containing at most two hetero atoms selected from O and S or simply a common side of a fused benzene ring.

The X may be a simple chemical bond or one member selected from the group consisting of —O—, —CO—, —SO$_2$—, —S—, —Rf'—, —(ORf')$_n$—, —(Rf'O)$_n$—, and —(ORf'O)$_n$— where Rf' is a perfluoroalkylene group, or a perfluoroarylene group, and n is an integer of 1 to 10.

The $R_2$ may be a divalent group having a structure represented by formula (4):

(4)

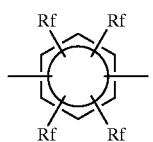

wherein Rf is a fluorine atom, a perfluoroalkyl group, a perfluoroaryl group, a perfluoroalkoxy group, or a perfluorophenoxy group.

The $R_2$ may also be a divalent group having a structure represented by formula (5):

(5)

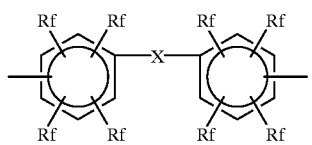

wherein Rf is a fluorine atom, a perfluoroalkyl group, a perfluoroaryl group, a perfluoroalkoxy group, or a perfluorophenoxy group; X is a simple chemical bond or one member selected from the group consisting of —O—, —CO—, —SO$_2$—, —S—, —Rf'—, —(ORf')$_n$—, —(Rf'O)$_n$—, and —(ORf'O)$_n$— where Rf' is a perfluoroalkylene group, or a perfluoroarylene group; and n is an integer of 1 to 10; or X and two (Rf)s adjacent thereto are combined and form, together with carbon atoms to which they are connected, a saturated or unsaturated, 5- or 6-membered ring containing at most two hetero atoms selected from O and S or simply a common periphery of a fused benzene ring.

The X may be a simple chemical bond or one member selected from the group consisting of —O—, —CO—, —SO$_2$—, —S—, —Rf'—, —(ORf')$_n$—, —(Rf'O)$_n$—, and —(ORf'O)$_n$— where Rf' is a perfluoroalkylene group, or a perfluoroarylene group, and n is an integer of 1 to 10.

The perfluorinated polyimide of the present invention has a structure in which all the monovalent elements connected to carbon atoms, alkyl groups, phenyl rings, etc. in the molecule are selected from fluorine and perfluorinated organic groups such as a perfluoroalkyl group, a perfluoroaryl group, a perfluoroalkoxy group, and a perfluorophenoxy group so as to exclude C—H bonds in the repeating unit, and as a result it is free of vibrational absorption due to C—H bonds which are a major cause for optical losses in near-infrared. Furthermore, presence of imido bonds in the main chain structure imparts the polyimide with a thermal resistance high enough to fabricate opto-electronic integrated circuits (260° C. or higher).

The perfluorinated polyimide of the present invention has an optical loss in an optical communication wavelength region much less than the conventional non-fluorinated or partially fluorinated polyimides.

Generally, the perfluorinated polyimide of the present invention is featured by having a low dielectric constant, a low refractive index, a low water absorption, a water or oil repellency, a low weatherability, a high oxygen permeability, a solvent solubility, and the like as well as a thermal resistance, and a light transmission ability in near-infrared region, and making use of such characteristic it can be applied to an electric material, an electronic material, a film material, a fiber material, a lubricant and the like.

The above and other objects, effects, features and advantages of the present invention will become more apparent from the following description of embodiments thereof taken in conjunction with the accompanying drawing.

DETAILED DESCRIPTION OF THE INVENTION

Figure 1:
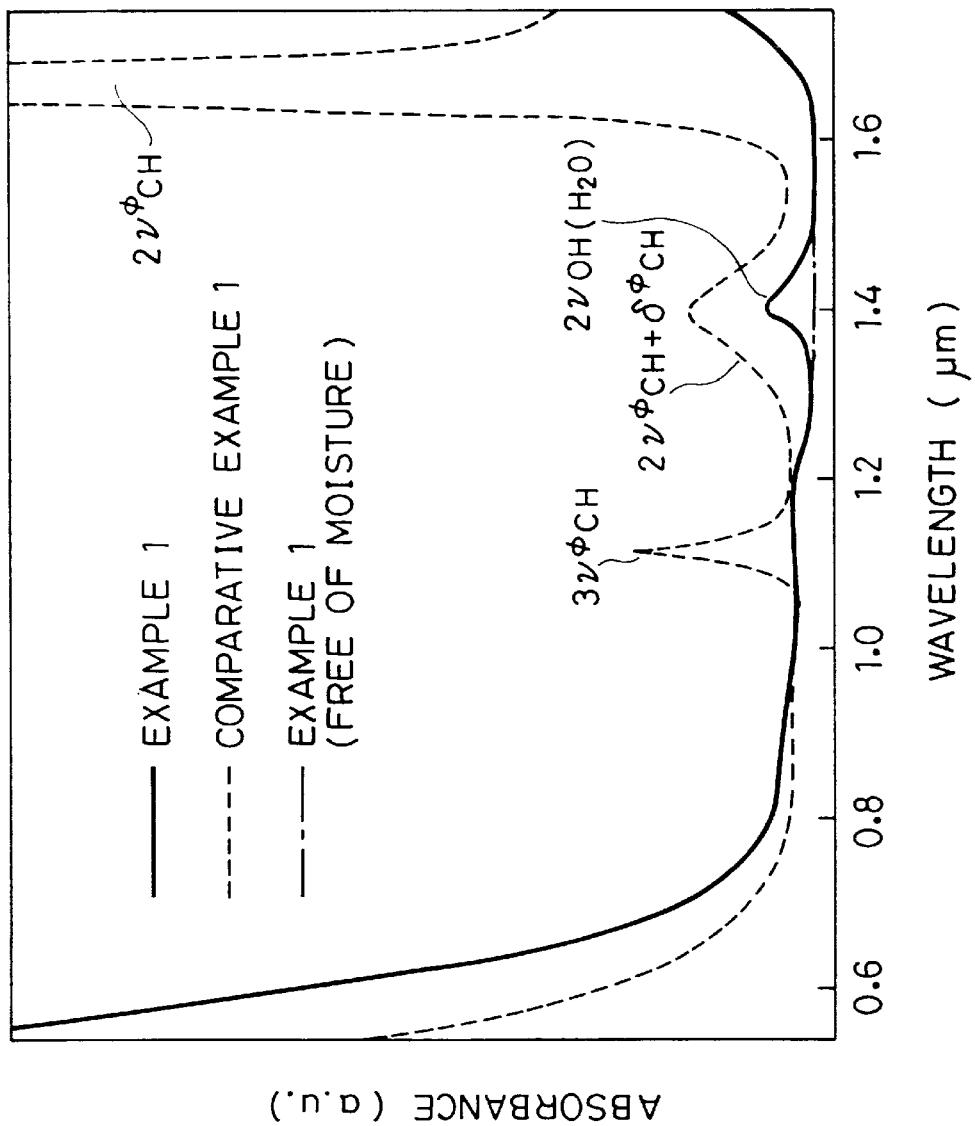
FIG. 1 is a graph illustrating dependence of absorbances of a perfluorinated polyimide according to Example 1 of the present invention and of a partially fluorinated polyimide according to Comparative Example 1, respectively, on wavelength, with a solid line indicating absorbance of the perfluorinated polyimide, a dotted line indicating absorbance of the partially fluorinated polyimide, and a dashed line indicating absorbance of the perfluorinated polyimide free of influence of absorption of moisture.

The perfluorinated polyimide of the present invention has a repeating unit represented by general formula (1):

(1)

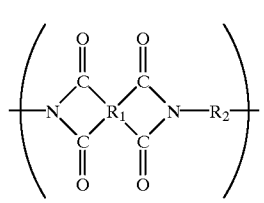

wherein $R_1$ is a tetravalent organic group; and $R_2$ is a divalent organic group, provided that chemical bonds between carbon atoms and monovalent elements contained in $R_1$ and $R_2$ are exclusively carbon-to-fluorine bonds.

The tetravalent organic group represented by $R_1$ may be a group having a structure represented by general formula (2):

(2)

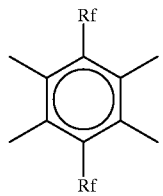

wherein Rf is a fluorine atom, a perfluoroalkyl group, a perfluoroaryl group, a perfluoroalkoxy group, or a perfluorophenoxy group.

Alternatively, the tetravalent organic group represented by $R_1$ may be a group having a structure represented by general formula (3):

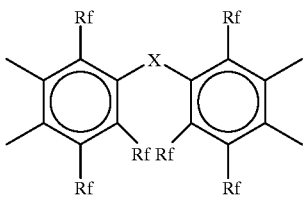

wherein Rf is a fluorine atom, a perfluoroalkyl group, a perfluoroaryl group, a perfluoroalkoxy group, or a perfluorophenoxy group; X is a simple chemical bond or one member selected from the group consisting of —O—, —CO—, —SO$_2$—, —S—, —Rf'—, —(ORf')$_n$—, —(Rf'O)$_n$—, and —(ORf'O)$_n$— where Rf' is a perfluoroalkylene group, or a perfluoroarylene group; and n is an integer of 1 to 10.

Further, X and two (Rf)s adjacent thereto may be combined and form together with carbon atoms to which they are connected a saturated or unsaturated, 5- or 6-membered ring containing at most two hetero atoms selected from O and S or simply a common periphery of a fused benzene ring.

The divalent organic group represented by R$_2$ may be a group having a structure represented by general formula (4):

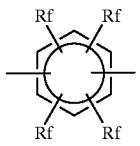

wherein Rf is a fluorine atom, a perfluoroalkyl group, a perfluoroaryl group, a perfluoroalkoxy group, or a perfluorophenoxy group.

The divalent organic group represented by R$_2$ may also be a group having a structure represented by general formula (5):

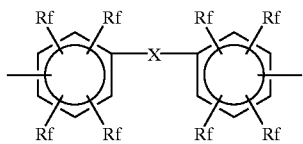

wherein Rf is a fluorine atom, a perfluoroalkyl group, a perfluoroaryl group, a perfluoroalkoxy group, or a perfluorophenoxy group; and X is a simple chemical bond or one member selected from the group consisting of —O—, —CO—, —SO$_2$—, —S—, —Rf'—, —(ORf')$_n$—, —(Rf'O)$_n$—, and —(ORf'O)$_n$— where Rf' is a perfluoroalkylene group, or a perfluoroarylene group; and n is an integer of 1 to 10.

Furthermore, X and two (Rf)s adjacent thereto may be combined and form together with carbon atoms to which they are connected a saturated or unsaturated, 5- or 6-membered ring containing at most two hetero atoms selected from O and S or simply a common periphery of a fused benzene ring.

In the formulae (2) through (5), the perfluoroalkyl group may have preferably 1 to 4 carbon atoms, and specific examples thereof include a trifluoromethyl group, a pentafluoroethyl group, a heptafluoropropyl group, a nonafluorobutyl group, etc.

The perfluoroaryl group may be, for example, a pentafluorophenyl group.

The perfluoroalkoxy group may have preferably 1 to 4 carbon atoms, and specific examples thereof include a trifluoromethoxy group, a pentafluoroethoxy group, a heptafluoropropoxy group, a nonafluorobutoxy group, etc.

The perfluoroalkylene group may have preferably 1 to 4 carbon atoms, and specific examples thereof include a difluoromethylene group, a tetrafluoroethylene group, a hexafluoroisopropylidene group, an octafluorobutylene group, etc.

The perfluoroarylene group may be, for example, a tetrafluoroarylene group.

In formulae (3) or (5) above, when X and two (Rf)s adjacent thereto together with carbon atoms to which they are connected are combined and form a ring, the resulting fused ring may have a ring skeleton, for example, an anthracene skeleton, an anthrone skeleton, a phenoxathiin skeleton, a thianthrene skeleton, a dibenz[b,e]1,4-dioxane skeleton, or the like. When X and two adjacent (Rf)s together with carbon atoms represent a common side of a fused ring, the ring skeleton represented by formula (3) or (5) is a naphthalene nucleus.

The perfluorinated polyimide represented by formula (1) above can be prepared by heating with cyclizing a poly(amic acid) represented by formula (6):

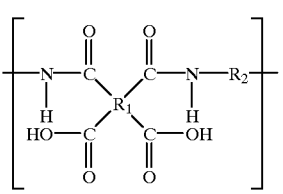

wherein R$_1$ and R$_2$ have the same meanings as defined above. The heat treatment may be carried out usually in air, preferably under nitrogen, at a temperature of 70 to 350° C. for 2 to 5 hours. More specifically, the heat treatment may preferably be carried out, for example, at 70° C. for 2 hours, 160° C. for 1 hour, 250° C. for 30 minutes, or 300° C. for 1 hour.

The perfluorinated poly(amic acid) represented by formula (6) used as a precursor for the preparation of is a novel, and can be prepared by reacting a tetracarboxylic acid dianhydride represented by formula (16):

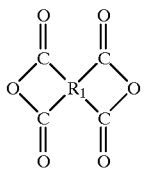

its corresponding tetracarboxylic acid or its reactive derivative, wherein R$_1$ has the same meaning as defined above, with a diamine represented by formula (17):

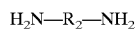

wherein R$_2$ has the same meaning as defined above.

As the tetracarboxylic acid or its reactive derivatives, there may be used any one in which all monovalent elements or monovalent functional groups bonded to carbon atoms in the molecule are selected from a fluorine atom, a perfluoroalkyl group, a perfluoroaryl group, a perfluoroalkoxy group, and a perfluorophenoxy group. The derivatives of the tetracarboxylic acid include acid anhydrides, acid chlorides, esters, etc.

Examples of the tetrafluorocarboxylic acid used in the present invention include 1,4-difluoropyromellitic acid, 1-trifluoromethyl-4-fluoropyromellitic acid, 1-pentafluoroethyl-4-fluoropyromellitic acid, 1-pentafluoroethyl-4-trifluoromethylpyromellitic acid, 1,4-di(pentafluoroethyl)pyromellitic acid, 1-pentafluorophenyl-4-fluoropyromellitic acid, 1-pentafluorophenyl-4-trifluoromethylpyromellitic acid, 1-pentafluorophenyl-4-pentafluoroethylpyromellitic acid, 1,4-di(pentafluorophenyl)pyromellitic acid, 1-trifluoromethoxy-4-fluoropyromellitic acid, 1-trifluoromethoxy-4-trifluoromethylpyromellitic acid, 1-trifluoromethoxy-4-pentafluoroethylpyromellitic acid, 1-trifluoromethoxy-4-pentafluorophenylpyromellitic acid, 1,4-di(trifluoromethoxy)pyromellitic acid, 1-pentafluoroethoxy-4-fluoropyromellitic acid, 1-pentafluoroethoxy-4-trifluoromethylpyromellitic acid, 1-pentafluoroethoxy-4-pentafluoroethylpyromellitic acid, 1-pentafluoroethoxy-4-pentafluoroethylpyromellitic acid, 1-pentafluoroethoxy-4-pentafluorophenylpyromellitic acid, 1-pentafluoroethoxy-4-trifluoromethoxypyromellitic acid, 1,4-di(pentafluoroethoxy)pyromellitic acid, 1-pentafluorophenoxy-4-fluoropyromellitic acid, 1-pentafluorophenoxy-4-trifluoromethylpyromellitic acid, 1-pentafluorophenoxy-4-pentafluoroethylpyromellitic acid, 1-pentafluorophenoxy-4-pentafluorophenylpyromellitic acid, 1-pentafluorophenoxy-4-trifluoromethoxypyromellitic acid, 1-pentafluorophenoxy-4-pentafluoroethoxypyromellitic acid, 1,4-di(pentafluorophenoxy)pyromellitic acid, hexafluoro-3,3',4,4'-biphenyltetracarboxylic acid, hexafluoro-3,3',4,4'-biphenylethertetracarboxylic acid, hexafluoro-3,3',4,4'-benzophenonetetracarboxylic acid, bis(3,4-dicarboxytrifluorophenyl) sulfone, bis(3,4-dicarboxytrifluorophenyl)sulfide, bis(3,4-dicarboxytrifluorophenyl)difluoromethane, 1,2-bis(3,4-dicarboxytrifluorophenyl)tetrafluoroethane, 2,2-bis(3,4-dicarboxytrifluorophenyl)hexafluoropropane, 1,4-bis(3,4-dicarboxytrifluorophenyl)tetrafluorobenzene, 3,4-dicarboxytrifluorophenyl-3',4'-dicarboxytrifluorophenoxydifluoromethane, bis(3,4-dicarboxytrifluorophenoxy)difluoromethane, 1,2-bis(3,4-dicarboxytrifluorophenoxy)tetrafluoroethane, 2,2-bis(3,4-dicarboxytrifluorophenoxy)hexafluoropropane, 1,4-bis(3,4-dicarboxytrifluorophenoxy)tetrafluorobenzene, 2,3,6,7-tetracarboxytetrafluoronaphthalene, 2,3,6,7-tetracarboxyhexafluoroanthracene, 2,3,6,7-tetracarboxyhexafluorophenanthrene, 2,3,6,7-tetracarboxytetrafluorobiphenylene, 2,3,7,8-tetracarboxytetrafluorodibenzofuran, 2,3,6,7-tetracarboxytetrafluoroanthraquinone, 2,3,6,7-tetracarboxypentafluoroanthrone, 2,3,7,8-tetracarboxytetrafluorophenoxathiin, 2,3,7,8-tetracarboxytetrafluorothianthrene, 2,3,7,8-tetracarboxytetrafluorodibenz[b,ee]1,4-dioxane, etc.; corresponding dianhydrides; corresponding chlorides; corresponding esters; and the like.

Among them, 1,4-di(trifluoromethyl)pyromellitic dianhydride, and 1,4-di(pentafluoroethyl)pyromellitic dianhydride, which are perfluorinated acid dianhydrides each having a chemical structure corresponding to pyromellitic dianhydride of which the benzene ring is substituted with a perfluoroalkyl group, can be prepared by the method described in Japanese Patent Application Laid Open No. Hei-2-15084. More particularly, durene is reacted with iodine in the presence of periodic acid to give diiododurene, which is then reacted with trifluoromethyl iodide or pentafluoroethyl iodide in the presence of copper to obtain 1,4-di(trifluoromethyl)durene or 1,4-di(pentafluoroethyl) durene. These compounds are then oxidized and dehydrated to obtain the aforementioned dianhydrides.

That is, pyromellitic dianhydride derivatives having a perfluoroalkyl group or a perfluoroaryl group can be prepared similarly as the above compounds by using, instead of trifluoromethyl iodide or pentafluoroethyl iodide, a corresponding perfluoroiodinated alkane or perfluoroiodinated arene.

Pyromellitic dianhydride derivatives having a trifluoromethoxy group or a pentafluoroethoxy group can be prepared according to the following reaction scheme-1.

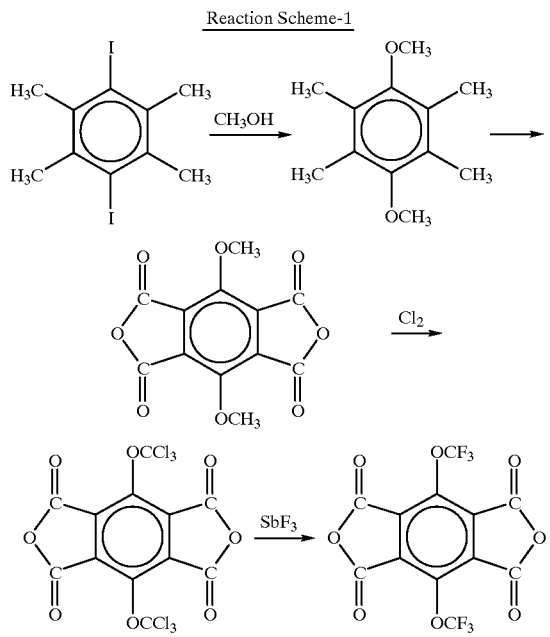

Similarly to the synthetic method of 3,6-diphenoxypyromellitic dianhydride as described by D. Brandelik, and W. A. Feld, ACS Polymer Preprint, 28(1), 88–89 (1987), those dianhydride compounds having a basic structure of pyromellitic dianhydride to which two perfluoro-tert-butyl groups or perfluorophenoxy groups are connected can be prepared by reacting diiododurene or dibromodurene with nonafluoro-tert-butyl alcohol or pentafluorophenol, hydrolyzing the product with an acid, and dehydrating the product.

Of the perfluorinated acid dianhydrides having a plurality of benzene rings represented by formula (12), those in which X is a simple chemical bond, or one of —O—, —CO—, —SO₂— or —S— can be prepared similarly to the industrial methods for preparing corresponding known acid dianhydrides in which all fluorine (F) atoms are replaced by hydrogen (H) atoms, with replacing the starting compounds (for example, phthalic anhydride, phthaloyl chloride, phthaloyl bromide, phthaloyl iodide, o-xylene, etc.) by corresponding perfluorinated compounds (for example, tetrafluorophthalic anhydride, trifluorophthaloyl chloride, trifluorophthaloyl bromide, trifluorophthaloyl iodide, tetrafluoro-o-xylene, etc.). Particularly, in the case where X is —O— or —S—, the objective compounds can be prepared using tetrafluorophthalonitrile as a starting compound by the following reaction scheme-2:

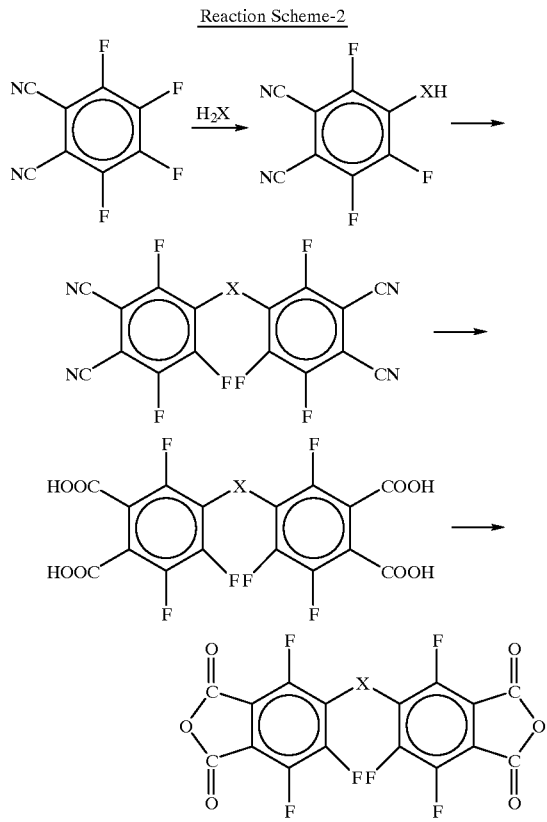

In the above formulae X is O or S.

Referring to the preparation method of 2,2-bis(3,4-dicarboxyphenyl)hexafluoropropane described in U.S. Pat. Nos. 3,356,648 and 3,959,350 to F. E. Rogers et al., and J. P. Critchley, P. A. Grattan, M. A. White, J. S. Pippett, *J. Polym. Sci.*, A-1, 10, 1789–1807 (1972) disclosing a preparation method of 1,3-bis(3,4-dicarboxyphenyl) hexafluoropropane, the perfluorinated dianhydrides having a plurality of benzene rings represented by formula (12) in which X is —Rf— where Rf is a perfluoroalkylene group or a perfluoroarylene group can be prepared similarly to the known acid anhydrides corresponding thereto in which all fluorine atoms are replaced by hydrogen atoms, with replacing the starting compounds (for example, phthalic anhydride, phthaloyl chloride, phthaloyl bromide, phthaloyl iodide, o-xylene, etc.) by corresponding perfluorinated compounds (for example, tetrafluorophthalic anhydride, trifluorophthaloyl chloride, trifluorophthaloyl bromide, trifluorophthaloyl iodide, tetrafluoro-o-xylene, etc.).

Of the perfluorinated acid dianhydrides having a plurality of benzene rings represented by formula (12), those in which X is —ORf'O— where Rf' is a perfluoroalkylene group or a perfluoroarylene group can be prepared in a manner similar to the method in which 1,4-bis(3,4-dicarboxytrifluorophenoxy)tetrafluorobenzene dianhydride of the present invention is prepared as explained hereinbelow, with replacing the starting compound, i.e., tetrafluorohydroquinone, by a corresponding perfluoroalkyldiol or dihydroxyperfluoroarene.

Of the perfluorinated acid dianhydrides having a plurality of benzene rings represented by formula (12), those in which X and two (Rf)s adjacent thereto are combined and form together with carbon atoms to which they are connected a saturated or unsaturated, 5- or 6-membered ring containing at most two hetero atoms selected from O and S can be prepared, for example, according to the following reaction scheme-3:

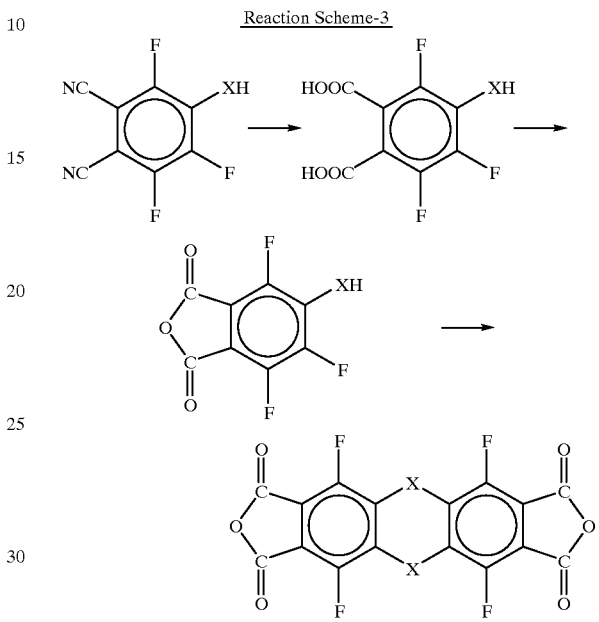

In the above formulae X is O or S.

As the diamine which can be used in the present invention, there may be cited any diamine in which all monovalent elements or monovalent functional groups bonded to carbon atoms in the molecule excepting amino groups are selected from the group consisting of a fluorine atom, a perfluoroalkyl group, a perfluoroaryl group, a perfluordalkoxy group, and a perfluorophenoxy group.

Specific examples of the diamine which can be used in the present invention include tetrafluoro-1,2-phenylenediamine, tetrafluoro-1,3-phenylenediamine, tetrafluoro-1,4-phenylenediamine, hexafluoro-1,5-diaminonaphthalene, hexafluoro-2,6-diaminonaphthalene, 3-trifluoromethyltrifluoro-1,2-phenylenediamine, 4-trifluoromethyltrifluoro-1,2-phenylenediamine, 2-trifluoromethyltrifluoro-1,3-phenylenediamine, 4-trifluoromethyltrifluoro-1,3-phenylenediamine, 5-trifluoromethyltrifluoro-1,3-phenylenediamine, 2-trifluoromethyltrifluoro-1,4-phenylenediamine, 3,4-bis(trifluoromethyl)difluoro-1,2-phenylenediamine, 3,5-bis(trifluoromethyl)difluoro-1,2-phenylenediamine, 2,4-bis(trifluoromethyl)difluoro-1,3-phenylenediamine, 4,5-bis(trifluoromethyl)difluoro-1,3-phenylenediamine, 2,3-bis(trifluoromethyl)difluoro-1,4-phenylenediamine, 2,5-bis(trifluoromethyl)difluoro-1,4-phenylenediamine, 3,4-bis(trifluoromethyl)difluoro-1,2-phenylenediamine, 3,4,5-tris(trifluoromethyl)fluoro-1,2-phenylenediamine, 3,4,6-tris(trifluoromethyl)fluoro-1,2-phenylenediamine, 2,4,5-tris(trifluoromethyl)fluoro-1,3-phenylenediamine, 2,4,6-tris(trifluoromethyl)fluoro-1,3-phenylenediamine, 4,5,6-tris(trifluoromethyli)fluoro-1,3-phenylenediamine, (trifluoromethyl)fluoro-1,3-phenylenediamine, tetrakis(trifluoromethyl)-1,2-phenylenediamine, tetrakis(trifluoromethyl)-1,3-phenylenediamine, tetrakis(trifluoromethyl)-1,4-phenylenediamine, 3-pentafluoroethyltrifluoro-1,2-phenylenediamine, 4-pentafluoroethyltrifluoro-1,2-phenylenediamine, 2-pentafluoroethyltrifluoro-1,3-phenylenediamine, 4-pentafluoroethyltrifluoro-1,3-phenylenediamine, 5-pentafluoroethyltrifluoro-1,3-phenylenediamine, 2-pentafluoroethyltrifluoro-1,4-phenylenediamine, 3-trifluoromethoxytrifluoro-1,2-phenylenediamine, 4-trifluoromethoxytrifluoro-1,2-phenylenediamine, 2-trifluoromethoxytrifluoro-1,3-phenylenediamine, 4-trifluoromethoxytrifluoro-1,3-phenylenediamine, 5-trifluoromethoxytrifluoro-1,3-phenylenediamine, 2-trifluoromethoxytrifluoro-1,4-phenylenediamine, 3,3'-diaminooctafluorobiphenyl, 3,4'-diaminooctafluorobiphenyl, 4,4'-diaminooctafluorobiphenyl, 2,2'-bis(trifluoromethyl)-4,4'-diaminohexafluorobiphenyl, 3,3'-bis(trifluoromethyl)-4,4'-diaminohexafluorobiphenyl, bis(3-aminotetrafluorophenyl)ether, 3,4'-diaminooctafluorobiphenyl ether, bis(4-aminotetrafluorophenyl)ether, 3,3'-diaminooctafluorobenzophenone, 3,4'-diaminooctafluorobenzophenone, 4,4'-diaminooctafluorobenzophenone, bis(3-aminotetrafluorophenyl) sulfone, 3,4'-diaminooctafluorobiphenyl sulfone, bis(4-aminotetrafluorophenyl)sulfone, bis(3-aminotetrafluorophenyl)sulfide, 3,4'-diaminooctafluorobiphenylsulfide, bis(4-aminotetrafluorophenyl)sulfide, bis(4-aminotetrafluorophenyl)difluoromethane, 1,2-bis(4-aminotetrafluorophenyl)tetrafluoroethane, 2,2-bis(4-aminotetrafluorophenyl)hexafluoropropane, 4,4''-diaminododecafluoro-p-terphenyl, 4-aminotetrafluorophenoxy-4'-aminotetrafluorophenyldifluoromethane, bis(4-aminotetrafluorophenoxy)difluoromethane, 1,2-bis(4-aminotetrafluorophenoxy)tetrafluoroethane, 2,2-bis(4-aminotetrafluorophenoxy)hexafluoropropane, 1,4-bis(4-aminotetrafluorophenoxy)tetrafluorobenzene, 2,6-diaminohexafluoronaphthalene, 2,6-diaminooctafluoroanthracene, 2,7-diaminooctafluorophenanthrene, 2,6-diaminohexafluorobiphenylene, 2,7-diaminohexafluorodibenzofuran, 2,6-diaminohexafluoroanthraquinone, 2,6-diaminooctafluoroanthrone, 2,7-diaminohexafluorophenoxathiin, 2,7-diaminohexafluorothianthrene, 2,7-diaminotetrafluorodibenz[b,e]1,4-dioxane, etc.

These diamines are known compounds or can be prepared by a known method or similarly thereto.

Among the aforementioned diamines, tetrafluoro-1,3-phenylenediamine, tetrafluoro-1,4-phenylenediamine, and 4,4'-diaminooctafluorobiphenyl are commercially available. Tetrafluoro-1,2-phenylenediamine can be prepared by the method described in I. L. Knunyants, G. G. Yakobson, "Synthesis of Fluoroorganic Compounds", Springer-Verlag, Berlin (1985); bis(4-aminotetrafluorophenyl)ether can be prepared by the method described in L. S. Kobrina, G. G. Furin, G. G. Yakobson, Zh. Obshch. Khim., 38, 514 (1968); bis(4-aminotetrafluorophenyl)sulfide can be prepared by the method described in G. G. Furin, S. A. Krupoder, G. G. Yakobson, Izv. Sib. Otd. Akad. Nauk. SSSR Ser. Khim. Nauk vyp. 5, 146 (1976). In examples hereinbelow, the aforementioned synthetic methods are followed. Other compounds than the aforementioned five specific compounds can be prepared, for example, by the following methods.

That is, of the perfluorinated diamine having a single benzene ring represented by general formula (13) above, those having a structure equivalent to one in which at most four fluorine atoms in a tetraphenylenediamine are replaced by a corresponding number of perfluoroalkyl or perfluoroaryl group can be synthesized by reacting a corresponding perfluoroiodinated alkane or perfluoroiodinated arene with tetrafluorophenylenediamine. Particularly, substitution reaction with a trifluoromethyl group is reported in Y. Kobayashi, I. Kumadaki, Tetrahedron Lett., 47, 4095–4096 (1969).

Of the perfluorinated diamine having a single benzene ring represented by general formula (13) above, those having a structure equivalent to one in which at most four fluorine atoms in a tetraphenylenediamine are replaced by a corresponding number of trifluoromethoxy group, or a pentafluoroethoxy group can be prepared by the following reaction scheme-4:

Reaction Scheme-4

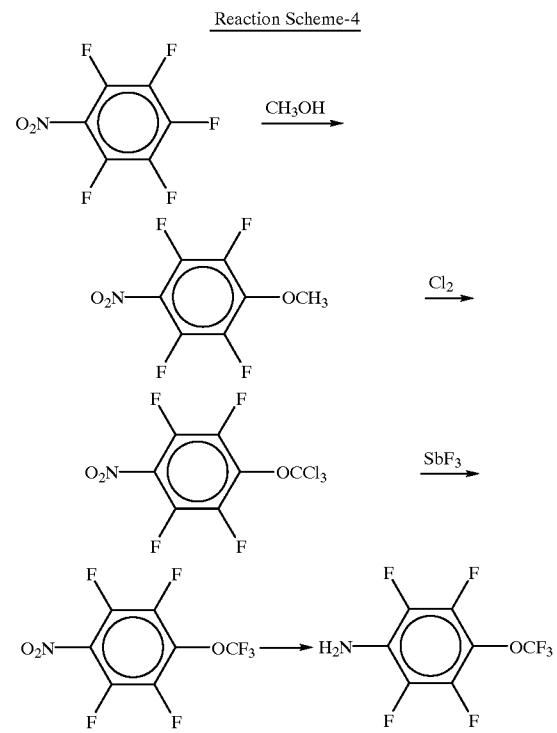

Of the perfluorinated diamines having a single benzene ring represented by general formula (13) above, those having a structure equivalent to one in which at most four fluorine atoms in a tetraphenylenediamine are replaced by a corresponding number of nonafluoro-tert-butoxy group, or a pentafluorophenoxy group can be prepared by reacting tetrafluorophenylenediamine with nonafluoro-tert-butyl alcohol or pentafluorophenol.

Of the perfluorinated diamines having a plurality of benzene rings represented by formula (14), those in which X is a simple chemical bond, or one of —O—, —CO—, —SO₂— or —S— can be prepared similarly to the industrial methods for preparing corresponding known diamines in which all fluorine (F) atoms are replaced by hydrogen (H) atoms, with replacing the starting compounds (for example, nitrobenzene, phenol, nitrophenol, chloronitrobenzene, bromonitrobenzene, iodonitrobenzene, etc.) by corresponding perfluorinated compounds (for example, pentafluoronitrobenzene, pentafluorophenol, tetrafluoronitrophenol, tetrafluorochloronitrobenzene, tetrafluorobromonitrobenzene, tetrafluoroiodonitrobenzene, etc.). Synthetic methods for these perfluorodiamines and their starting compounds are described in the aforementioned publication by I. L. Knunyants, et al.

Referring to the preparation methods of 2,2-bis(4-aminophenyl)hexafluoropropane and of 2,2-bis(3-aminophenyl)hexafluoropropane described in U.S. Pat. Nos. 3,356,648 and 3,959,350 to F. E. Rogers et al., the perfluorinated diamines having a plurality of benzene rings represented by formula (14) in which X is —Rf— where Rf is a perfluoroalkylene group or a perfluoroarylene group can be prepared similarly to the known diamines corresponding thereto in which all fluorine atoms are replaced by hydrogen atoms, with replacing the starting compounds (for example, nitrobenzene, phenol, nitrophenol, chloronitrobenzene, bromonitrobenzene, iodonitrobenzene, etc.) by corresponding perfluorinated compounds (for example, pentafluoronitrobenzene, pentafluorophenol, tetrafluoronitrophenol, tetrafluorochloronitrobenzene, tetrafluorobromonitrobenzene, tetrafluoroiodonitrobenzene, etc.).

Of the perfluorinated diamines having a plurality of benzene rings represented by formula (14), those in which X is —ORfO— where Rf is a perfluoroalkylene group or a perfluoroarylene group can be prepared, for example, by the following reaction scheme-5:

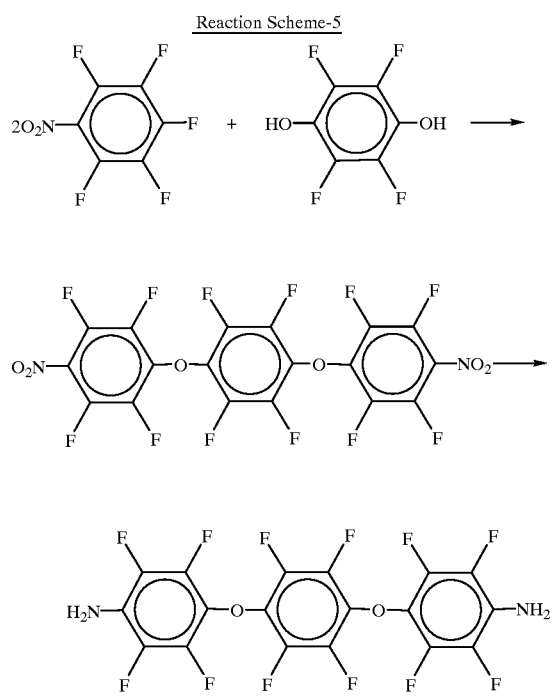

Of the perfluorinated diamines having a plurality of benzene rings represented by formula (14), those in which X and two (Rf)s adjacent thereto are combined and form together with carbon atoms to which they are connected a saturated or unsaturated, 5- or 6-membered ring containing at most two hetero atoms selected from O and S can be prepared, for example, according to the following reaction scheme-6:

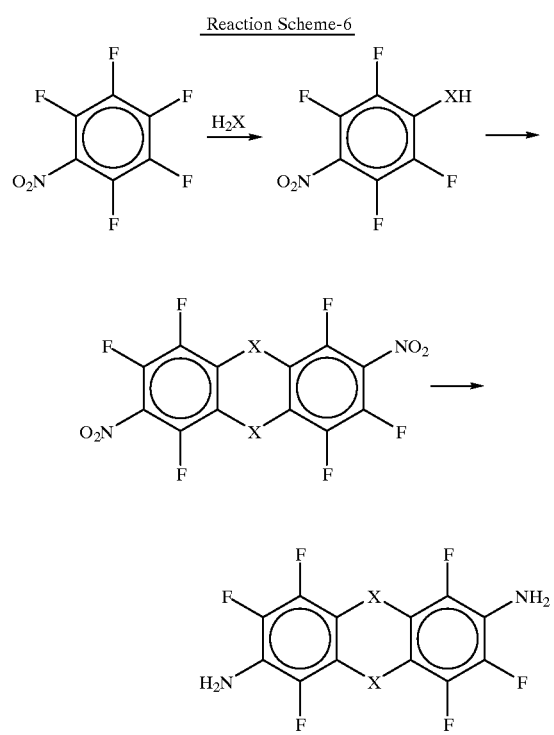

In the above formulae X is O or S.

The preparation of the poly(amic acid) used as a precursor for preparing the perfluorinated polyimide of the present invention can be performed generally in a polar organic solvent such as N-methyl-2-pyrrolidone, N,N-dimethylacetamide, and N,N-dimethylformamide. The reaction may be performed usually at room temperature for 7 days or longer under a dry nitrogen atmosphere.

In the present invention, diamines or tetracarboxylic dianhydrides may be used singly or two or more of them may be used in combination. In these cases, the molar amount of the single diamine or total molar amount of two or more diamines is set equal or almost equal to the molar amount of the single tetracarboxylic anhydride or total molar amount of two or more tetracarboxylic dianhydrides.

As for the polymerization solutions such as a solution of poly(amic acid), the concentration thereof may be generally 5 to 40% by weight, preferably 10 to 25% by weight. The polymer solution may suitably have a rotation viscosity at 25° C. of 50 to 500 poises.

Among the starting compounds which can be used for preparing the perfluorinated polyimide and perfluorinated poly(amic acid) of the present invention, preferred are perfluorinated aromatic compounds represented by general formula (7):

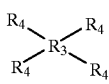

(7)

wherein $R_3$ is a tetravalent perfluorinated aromatic group represented by formula (8) or (9):

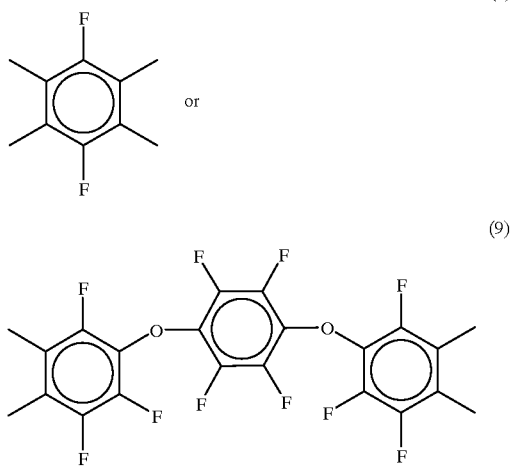

(8)

(9)

and four ($R_4$)s are same, each being a carboxyl group or a cyano group, or two adjacent ($R_4$)s combine to form a divalent group represented by formula (10):

(10)

provided that when $R_4$ is a cyano group, $R_3$ denotes the tetravelent perfluorinated aromatic group represented by formula (9).

The perfluorinated aromatic compounds are novel and include 1,4-bis(3,4-dicarboxytrifluorophenoxy)tetrafluorobenzene dianhydride, 1,4-difluoropyromellitic dianhydride, 1,4-bis(3,4-dicarboxytrifluorophenoxy)tetrafluorobenzene, 1,4-difluoropyromellitic acid, and 1,4-bis(3,4-dicyanotrifluorophenoxy)tetrafluorobenzene. These compounds can be prepared according to reaction scheme-7 or reaction scheme-8 below.

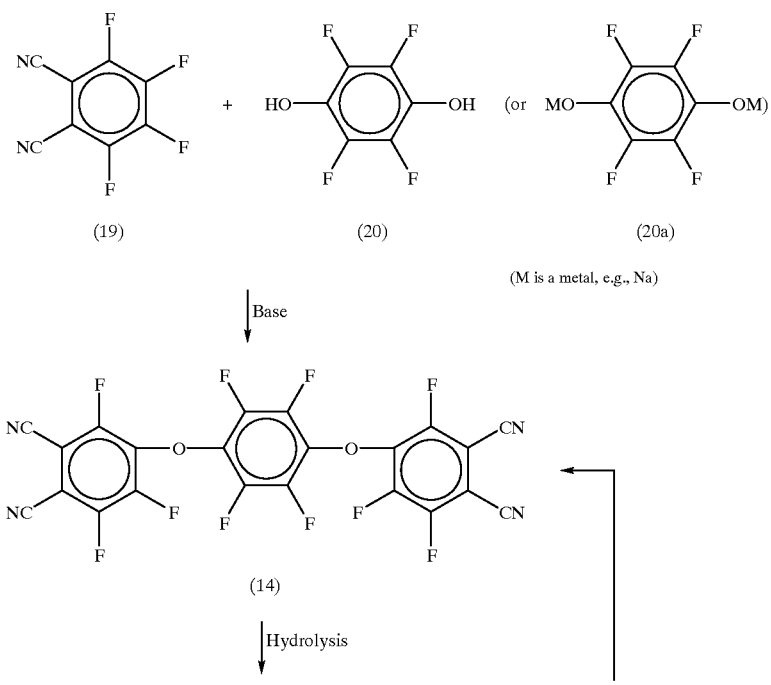

-continued

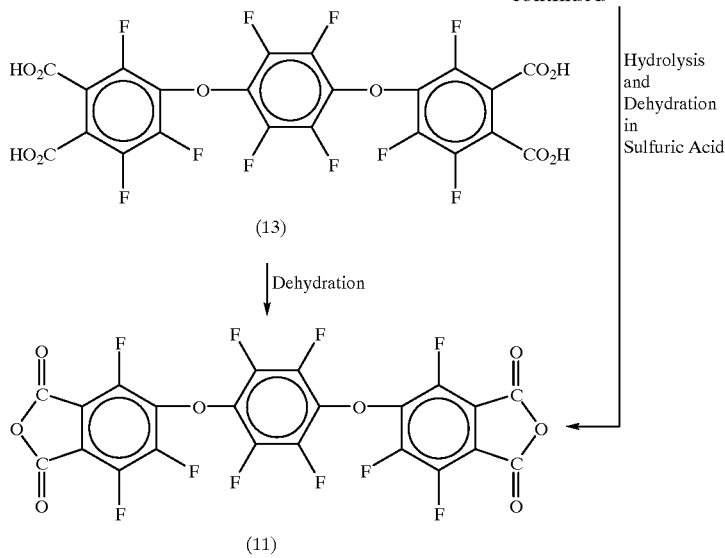

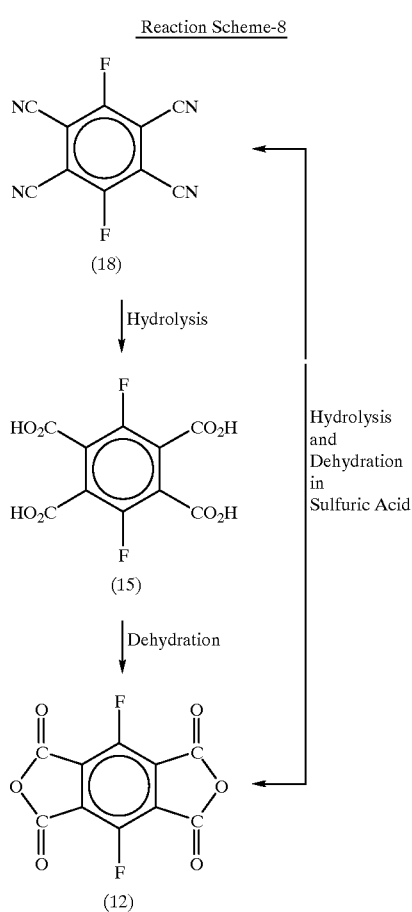

More specifically, in Reaction Scheme-7, tetrafluorophthalonitrile and tetrafluorohydroquinone (or its metal salts, e.g., disodium salt) are reacted usually in the presence of a base (for example, trimethylamine, etc.) in a polar solvent at 0 to 5° C. for 30 minutes to obtain 1,4-bis(3,4-dicyanotrifluorophenoxy)tetrafluorobenzene, which is then hydrolyzed, for example, in an aqueous 60% sulfuric acid solution at 150° C. for 15 hours to obtain 1,4-bis(3,4-dicarboxytrifluorophenoxy)tetrafluorobenzene. Refluxing the product in acetic anhydride for 2 hours results in dehydration to give 1,4-bis(3,4-dicarboxytrifluorophenoxytetrafluorobenzene dianhydride. Also, 1,4-bis(3,4-dicyanotrifluorophenoxy)tetrafluorobenzene may be heated, for example, in an aqueous 80% sulfuric acid solution at 200° C. for 2 hours to effect hydrolysis and dehydration in one step to obtain 1,4-bis(3, 4-dicarboxytrifluorophenoxytetrafluorobenzene dianhydride.

In Reaction Scheme-8, 1,4-difluorotetracyanobenzene is hydrolyzed, for example under the conditions of 150° C. for 15 hours in an aqueous 60% sulfuric acid solution to obtain 1,4-difluoropyromellitic acid. On the other hand, 1,4-difluorotetracyanobenzene may be heated, for example, under the conditions of at 200° C. for 2 hours in an aqueous 80% sulfuric acid solution to effect hydrolysis and dehydration in one step to obtain 1,4-difluoropyromellitic dianhydride.

Films of the perfluorinated polyimide of the present invention can be prepared by a conventional method for fabricating polyimide films. For example, a suitable solution of the perfluorinated poly(amic acid) of the present invention is spin-coated on an aluminum plate and heated from 70° C. to 350° C. stepwise (70° C. for 2 hours, 160° C. for 1 hour, 250° C., for 30 minutes, and then 350° C. for 1 hour) to effect imidization. Thereafter, the aluminium plate thus coated is immersed in 10% hydrochloric acid to dissolve the aluminum plate itself to obtain a perfluorinated polyimide film.

EXAMPLES

Hereafter, the present invention will be described in greater detail by way of examples. However, the present invention should not be construed as being limited thereto.

In the following examples and comparative example, imidization was confirmed by characteristic absorptions due to symmetric or asymmetric stretching vibration of carbonyl groups in infrared absorption spectrum. Light transmission was determined by the measurement of visible light-near infrared absorption spectrum. Thermal decomposition temperature (10% weight loss temperature) was measured using a thermogravimeter in a nitrogen stream at a temperature elevation rate of 10° C./minute. Glass transition temperature was measured using a thermodynamic analyzer in a nitrogen stream under a load of 5 g and at a temperature elevation rate of 5° C./minute. Dielectric constant was measured at a frequency of 1 kHz using a dielectric constant measurement apparatus by an air-gap method. Water absorption was calculated from change in weight when a 20 μm thick film was dipped in water at 23° C. for 7 days. Refractive indices at wavelengths of 0.633 μm, 1.320 μm, and 1.523 μm were measured using a prism coupler with helium neon laser and laser diodes as light sources. Since polyimides generally show birefringence and the refractive index in between in-plane direction ($n_{TE}$) and the refractive index in a direction normal to the plane ($n_{TM}$), linearly polarized light was used to measured $n_{TE}$ and $n_{TM}$, respectively.

Abbreviations and chemical formulae for compounds used in the preparation of perfluorinated poly(amic acid)s and perfluorinated polyimides in the examples are as indicated below:

10FEDA: 1,4-Bis(3,4-dicarboxytrifluorophenoxy) tetrafluorobenzene dianhydride

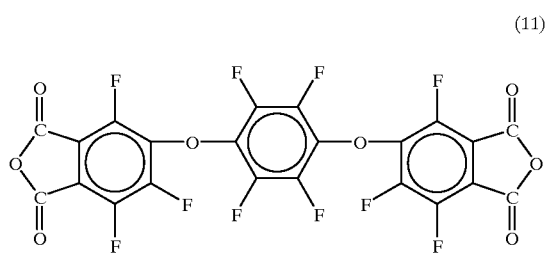

(11)

P2FDA: 1,4-Difluoropyromellitic dianhydride

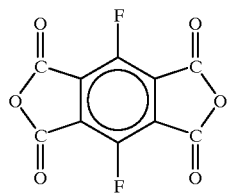

(12)

P6FDA: 1,4-Bis(trifluoromethyl)pyromellitic dianhydride

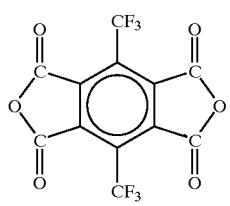

(21)

4FMPD: Tetrafluoro-1,3-phenylenediamine

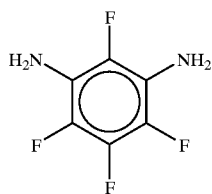

(22)

4FPPD: Tetrafluoro-1,4-phenylenediamine

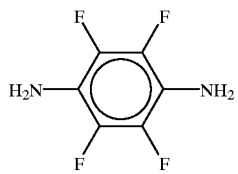

(23)

8FODA: Bis(4-aminotetrafluorophenyl)ether

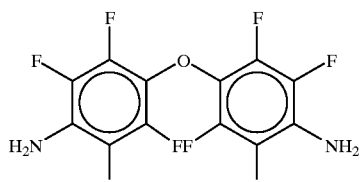

(24)

8FSDA: Bis(4-aminotetrafluorophenyl)sulfide

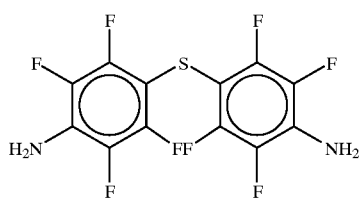

(25)

It should be noted that 10FEDA and P2FDA are novel compounds.

Example 1

In an Erlenmeyer flask were charged 11.644 g (20.0 mmol) of 10FEDA of formula (1) above purified by sublimation under reduced pressure, 3.602 g (20.0 mmol) of 4FMPD of formula (4) above purified by sublimation under reduced pressure, and 86 g of N,N-dimethylacetamide (DMAc). The solution obtained was stirred at room temperature for 7 days under nitrogen atmosphere to obtain a solution of a perfluorinated poly(amic acid) in DMAc. The DMAc solution was spin-coated on an aluminum plate and heated stepwise at 70° C. for 2 hours, at 160° C. for 1 hour, at 250° C. for 30 minutes, and then at 350° C. for 1 hour to imidize the poly(amic acid). The sample thus obtained was immersed in an aqueous 10% hydrochloric acid solution to dissolve the aluminum plate to release a polyimide film. Infrared absorption of the polyimide film thus obtained was measured, and the spectrum indicated appearance of an absorption specific to an imido group at 1790 cm$^{-1}$, which confirmed that the imidization pr6ceeded completely. Then optical absorption of the polyimide film over a wavelength region, of, from 0.8 to 1.7 µm was measured and the results obtained are illustrated in FIG. 1, in which vertical and horizontal axes stand for absorbance (arbitrary unit) and wavelength (µm), respectively, and a solid line indicates wavelength-dependence of absorbance of the perfluorinated polyimide obtained in Example 1, and a dotted line indicates wavelength-dependence of absorbance of the partially fluorinated polyimide obtained in Comparative Example 1 hereinbelow, and a dashed line indicating absorbance of the perfluorinated polyimide free of influence of absorption of moisture adhering to the film. As illustrated in FIG. 1, no substantial absorption peak appeared in the optical communication wavelength region except for a low absorption peak due to the moisture derived from the moisture in the air and adhering to the film.

Figure 2:
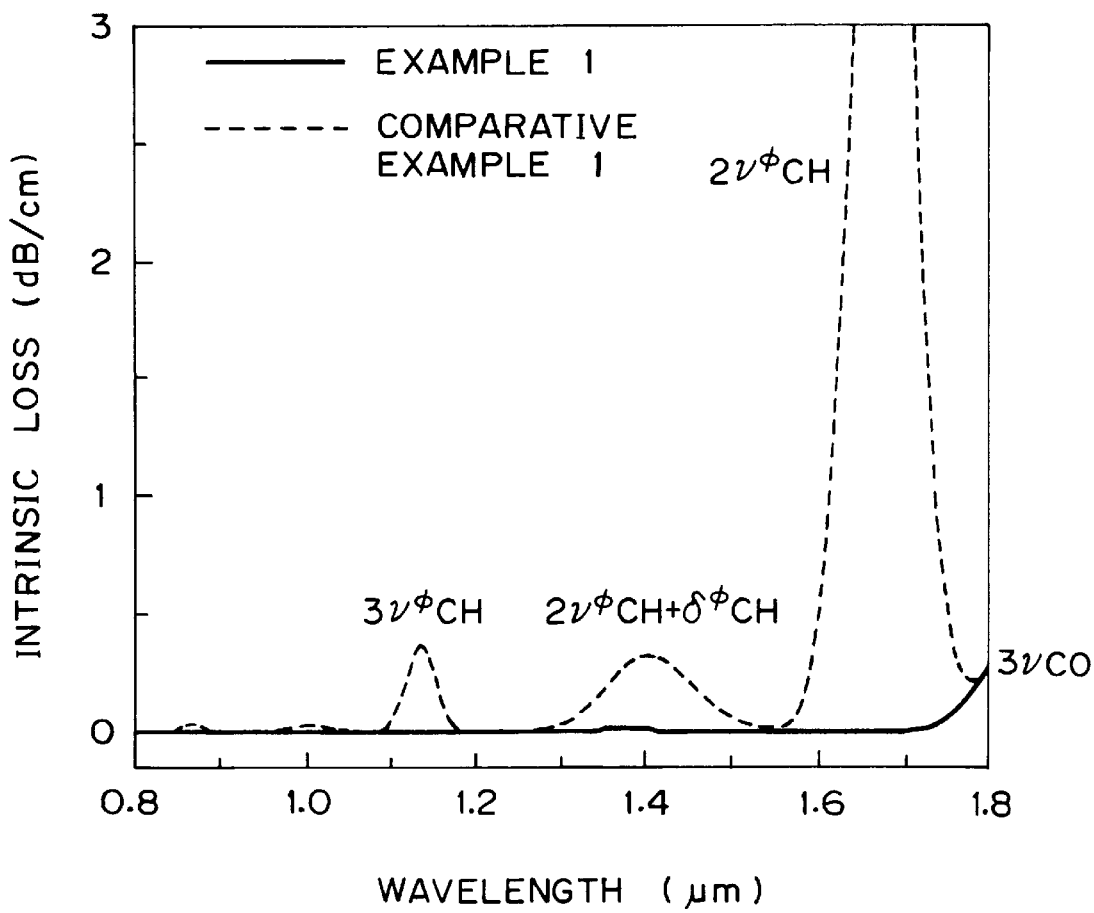
FIG. 2 is a graph of intrinsic loss (dB/cm) of a perfluorinated polyimide according to Example 1 of the present invention and of a partially fluorinated polyimide according to comparative Example 1, respectively with wavelength.

Then, in order to evaluate intrinsic loss specific to the perfluorinated polyimide material in the visible-infrared region, the intrinsic loss over a wavelength range of 0.8 to 1.8 µm was calculated according to the method of W. Grob described in W. Groh, *Macromolecul. Chem.*, Vol. 189, (1988) p. 2861, and the results obtained are illustrated in FIG. 2, in which vertical and horizontal axes stand for intrinsic loss (dB/cm) and wavelength (µm), respectively. The intrinsic loss spectrum obtained by calculation corresponded well to the absorption spectrum shown in FIG. 1. Hence, it is presumed that the perfluorinated polyimide showed no absorption peak within the range of 0.8 to 1.7 µm, and that the intrinsic loss did not exceed 0.1 dB/cm within this wavelength range. Note that in a wavelength region slightly longer than 1.8 µm, there exists a peak due to a third harmonic of a stretching vibration of the C=O bond in an imide group. The "skirt" of the absorption appearing at a wavelength not shorter than 1.7 µm in FIG. 1 would be attributed to this absorption. The polyimide had a thermal decomposition temperature of 501° C., a glass transition temperature of 309° C., a dielectric constant of 2.8, and a water absorption of 0.2%. Also, the perfluorinated polyimide had a refractive index $n_{TE}$=1.5565 and $n_{TM}$=1.5529, respectively, at a wavelength of 0.633 µm; $n_{TE}$=1.5318 and $n_{TM}$=1.5289, respectively, at a wavelength of 1.320 µm; and $n_{TE}$=1.5295 and $n_{TM}$=1.5265, respectively at a wavelength of 1.523 µm. The birefringence of the perfluorinated polyimide was about 0.0030 to 0.0036, which was smaller than the birefringences of conventional polyimides and fluorinated polyimides.

Example 2

The procedure of Example 1 was repeated except that instead of 4FMPD there was used 6.88 g (20.0 mmol) of 8FODA of formula (6) above purified by sublimation, and 105 g of N,N-dimethylacetamide (DMAc) was added thereto to obtain a corresponding perfluorinated polyimide. Measurement was made of the optical absorption of the perfluorinated polyimide thus obtained within an optical communication wavelength region of 0.8 to 1.7 µm. As a result, there was observed no peak other than a slight absorption attributed to moisture in the air, as in Example 1. The perfluorinated polyimide had a thermal decomposition temperature of 485° C., a glass transition temperature of 300° C., a dielectric constant of 2.6, and a water absorption of 0.2%. Further, the perfluorinated polyimide had a refractive index $n_{TE}$=1.5468 and $n_{TM}$=1.5378, respectively, at a wavelength of 0.633 µm; $n_{TE}$=1.5320 and $n_{TM}$=1.5150, respectively, at a wavelength of 1.320 µm; and $n_{TE}$=1.5211 and $n_{TM}$=1.5133, respectively, at a wavelength of 1.523 µm. The birefringence of the perfluorinated polyimide was about 0.0078 to 0.0090.

Example 3

The procedure of Example 1 was repeated except that instead of 4FMPD there was used 7.20 g (20.0 mmol) of 8FSDA of formula (7) above purified by sublimation, and 107 g of N,N-dimethylacetamide (DMAC) was added thereto to obtain a corresponding perfluorinated polyinide. Measurement was made of the optical absorption of the perfluorinated polyimide thus obtained within an optical communication wavelength region of 0.8 to 1.7 µm. As a result, there was observed no peak other than a slight absorption attributed to moisture in the air, as in Example 1. The perfluorinated polyiniide had a thermal decomposition temperature of 488° C., a glass transition temperature of 278° C., a dielectric constant of 2.6, and a water absorption of 0.3%. Further, the perfluorinated polyimide had a refractive index $n_{TE}$=1.5548 and $n_{TM}$=1.5458, respectively, at a wavelength of 0.633 µm; $n_{TE}$=1.5310 and $n_{TM}$=1.5230, respectively, at a wavelength of 1.320 µm; and $n_{TE}$=1.5291 and $n_{TM}$=1.5223, respectively, at a wavelength of 1.523 µm. The birefringence of the pertluorinated polyimide was about 0.0068 to 0.0090.

Examples 4 to 12

Perfluorinated poly(amic acid) solutions and perfluorinated polyimides were prepared in the same manner as in Example 1 for all combinations of three types of tetracarboxylic dianhydrides (each 20.0 mmol) with four types of diamines (each 20.0 mmol) minus the combination used in Example 1 to 3 to obtain products of Examples 4 to 12, respectively. The types and amounts of the starting compounds as well as amount of the solvent used are described in Table 1. Optical absorption spectrum of each of the polyimide films obtained was measured in an optical communication wavelength region of 0.8 to 1.7 µm, and as a result it revealed that no peak was found other than a low absorption peak due to moisture adhering to the films as in Example 1. These perfluorinated polyimides had thermal decomposition temperatures and glass transition temperatures all higher than the 260° C. soldering temperature. They had dielectric constants not higher than 2.8 and water absorption not higher than 0.3%.

Comparative Example 1

In an Erlenmeyer flask were charged 8.885 g (20.0 mmol) of 2,2-bis(3,4-dicarboxyphenyl)hexafluoropropane dianhydride having the following structural formula:

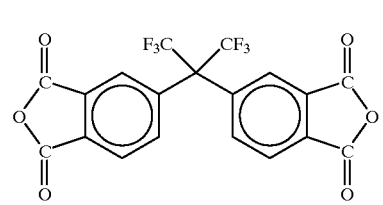

(26)

6.405 g (20.0 mmol) of 2,2'-bis(trifluoromethyl)-4,4'-diaminobiphenyl having the following structural formula:

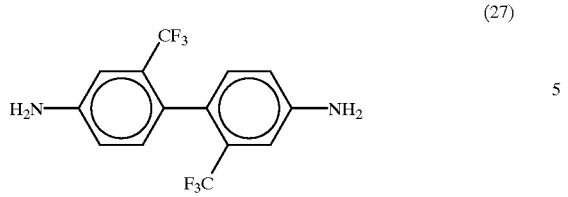

(27)

and 87 g of N,N-dimethylacetamide (DMAc) and the mixture was treated in the same manner as in Example 1 to obtain a polyimide film. Optical absorption of the polyimide film thus obtained was measured within a wavelength region of 0.8 to 1.7 $\mu$m, and the results obtained are illustrated in FIG. 1, in which a dotted line indicates the absorption of the polyimide film of Comparative Example 1. As indicated by the dotted line in FIG. 1, absorption peak due to 3-fold overtone of the stretching vibration of C—H bond appeared at near 1.1 $\mu$m. At near 1.4 $\mu$m there appeared an absorption peak due to combination of a harmonic of stretching vibration of C—H bond and a deformation vibration of C—H bond while there appeared at near 1.65 $\mu$m an absorption peak due to 2-fold overtone of stretching vibration of C—H bond.

From the calculated spectra illustrated in FIG. 2, it is presumed that intrinsic losses near 1.1 $\mu$m and near 1.4 $\mu$m are about 0.3 dB/cm, and an intrinsic loss near 1.63 $\mu$m is not lower than 20 dB/cm. It can be seen therefore that there is an intrinsic loss of not lower than 0.1 dB/cm over a relatively wide range of wavelength due to the influence of the absorption peaks inherent to the materials.

From these results it is clear that the perfluorinated polyimide of the present invention has an optical loss considerably lower than that of the conventional partially fluorinated polyimide in the aforementioned optical communication wavelength region.

The perfluorinated polyimides obtained in Examples 1 to 12 and the fuorinated polyimide prepared in Comparative Example 1 have chemical structures having repeating units represented by the following formulae, respectively:

Example 1: 10FEDA/4FMPD

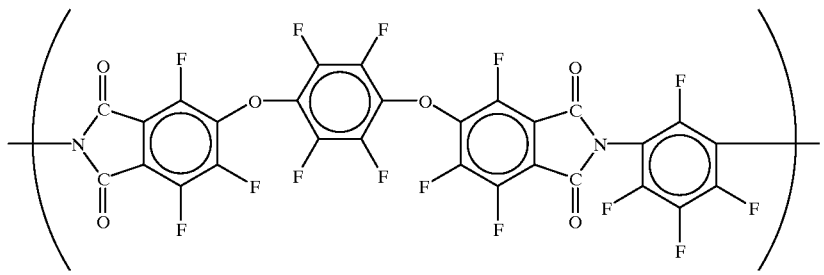

Example 2: 10FEDA/4FPPD
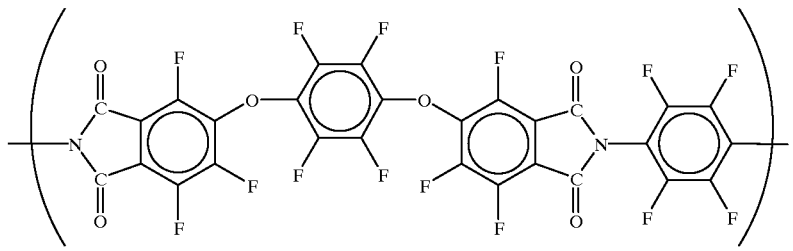
Example 3: 10FEDA/8FODA
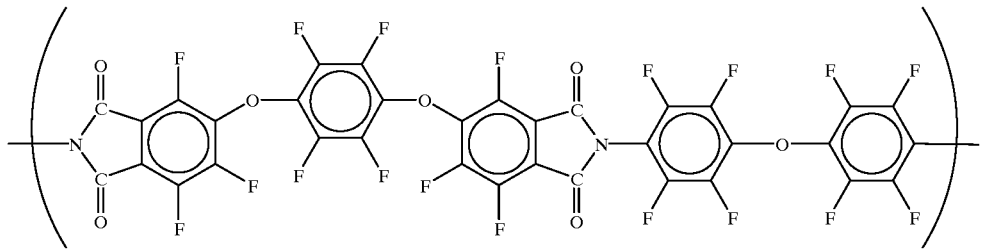
Example 4: 10FEDA/8FSDA
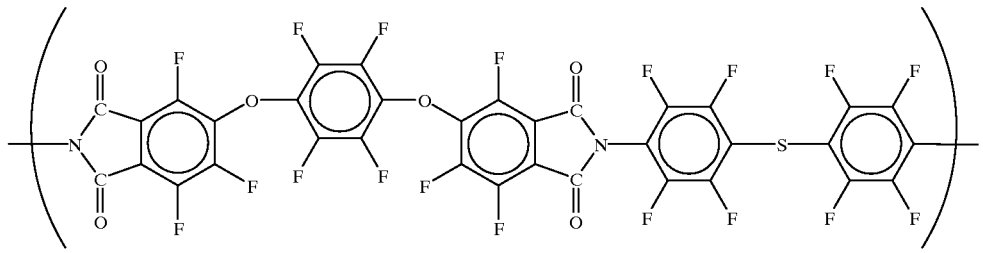
Example 5: P2FDA/4FMPD
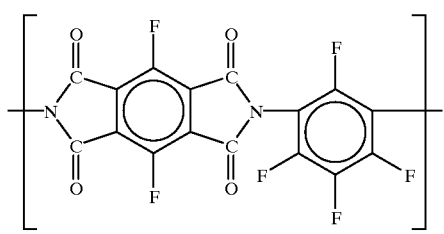
Example 7: P2FDA/8FODA
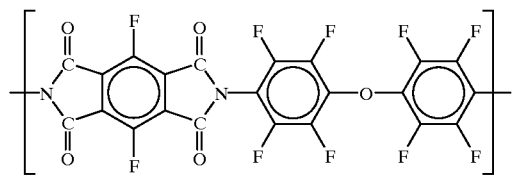
Example 6: P2FDA/4FPPD
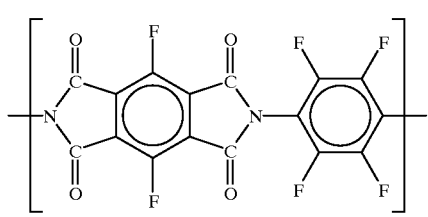
Example 8: P2FDA/8FSDA
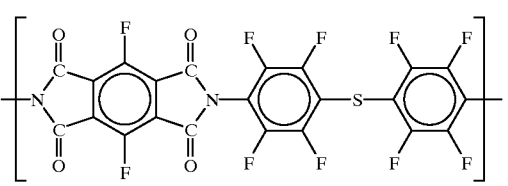

Example 9: P6FDA/4FMPD

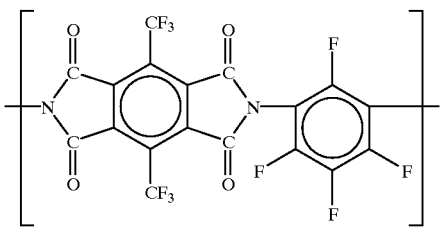

Example 10: P6FDA/4FPPD

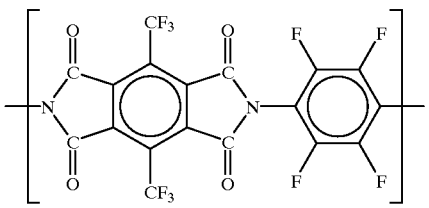

Example 11: P6FDA/8FODA

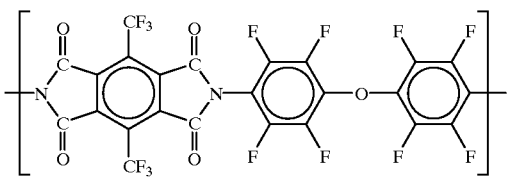

Example 12: P6FDA/8FSDA

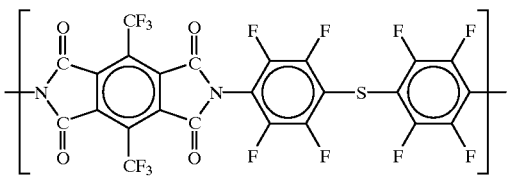

Comparative Example 1: 6FDA/TFDB

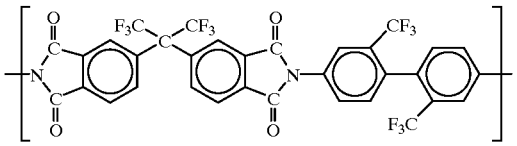

Example 13

In an eggplant type flask were charged 6.18 g (10 mmol) of 1,4-bis(3,4-dicarboxytrifluorophenoxy) tetrafluorobenzene and 20.4 g (0.2 mol) of acetic anhydride. The mixture was reacted under reflux for 2 hours. After completion of the reaction, the flask was left to stand to decrease the temperature of the contents down to room temperature. White solids which precipitated were filtered and dried to obtain 5.25 g of a product in a yield of 90% as 1,4-bis(3,4-dicarboxytrifluorophenoxy)tetrafluorobenzene dianhydride. Upon infrared absorption spectroscopy of the product, absorption at 2,500 to 3,700 cm$^{-1}$ due to a hydroxyl group in carboxylic acid and absorption at near 1,750 cm$^{-1}$ due to a carbonyl group observed on 1,4-bis(3,4-dicarboxytrifluorophenoxy)tetrafluorobenzene disappeared and instead absorptions at 1,880 cm$^{-1}$ and 1,790 cm$^{-1}$, respectively, specific to a carbonyl group of an acid anhydride, appeared.

Upon measurement of proton nuclear magnetic resonance ($^1$H-NMR) spectrum using deuterated dimethyl sulfoxide (DMSO-d$_6$) as a solvent and tetramethylsilane (TMS) as an internal standard, signal (13.2 ppm) due to hydrogen in a carboxylic acid observed on 1,4-bis(3,4-dicarboxytrifluorophenoxy)tetrafluorobenzene disappeared and no signal was observed. Similarly, measurement of fluorine nuclear magnetic resonance ($^{19}$F-NMR) spectrum of the product was performed using DMSO-d$_6$ as a solvent and CFCl$_3$ as an internal standard, and as a result four signals were observed whose integral ratio was 4:2:2:2 from the upfield side.

In elemental analysis of the product, calculated value of carbon was 45.39% while found value was 45.18% and well corresponded to the calculated value.

From the above results, the compound obtained as a result of this reaction was confirmed to be 1,4-bis(3,4-dicarboxyphenoxy)tetrafluorobenzene dianhydride, the objective compound.

Example 14

In an eggplant type flask were charged 5.42 g (10 mmol) of 1,4-bis(3,4-dicyanotrifluorophenoxy)tetrafluorobenzene and 10 ml of 80% sulfuric acid, and the mixture was stirred at 200° C. for 2 hours. After completion of the reaction, the flask was left to stand to decrease the temperature of the contents down to room temperature. White solids which precipitated were filtered and quickly washed with deionized water, followed by drying to obtain 5.06 g of a product in a yield of 87% as 1,4-bis-(3,4-dicarboxytrifluorophenoxy) tetrafluorobenzene dianhydride. In the same manner as in Example 13, the product was confirmed to be 1,4-bis(3,4-dicarboxytrifluorophenoxy)tetrafluorobenzene dianhydride, the objective compound.

Example 15

In an eggplant type flask were charged 5.42 g (10 mmol) of 1,4-bis(3,4-dicyanotrifluotophenoxy)tetrafluorobenzene and 10 ml of 60% sulfuric acid. The mixture was reacted at 150° C. for 15 hours. After completion of the reaction, the flask was left to stand to decrease the temperature thereof down to room temperature. White solids which precipitated were filtered and washed with water sufficiently. The solids were dried at 100° C. under vacuum to obtain 5.62 g of a white product in a yield of 91% as 1,4-bis(3,4-dicarboxytrifluorophenoxy)tetrafluorobenzene. Upon infrared absorption spectroscopy of the product, absorption at 2,250 cm$^{-1}$ due to a cyano group observed on 1,4-bis(3,4-dicyanotrifluorophenoxy)tetrafluorobenzene disappeared and an absorption at 2,500 to 3,700 cm$^{-1}$ due to a hydroxyl group in a carboxylic acid and an absorption at near 1,750 cm$^{-1}$ due to a carbonyl group in a carboxylic acid appeared newly.

Upon measurement of $^1$H-NMR spectrum in DMSO-d$_6$ using TMS as an internal standard, a signal due to a hydroxyl group in a carboxylic acid appeared at 13.2 ppm. In $^{19}$F-

NMR analysis in DMSO-$d_6$ using $CFCl_3$ as an internal standard, four signals were observed whose integral ratio was 4:2:2:2 from the upfield side.

In elemental analysis of the product, calculated values of carbon and hydrogen were 42.74% and 0.65%, respectively, while found values thereof were 42.50% and 0.63%, respectively, and well corresponded to the calculated values.

From the above results, the compound obtained as a result of this reaction was confirmed to be 1,4-bis(3,4-dicarboxytrifluorophenoxy)tetrafluorobenzene the objective compound.

Example 16

In an Erlenmeyer flask were charged 4.0 g (20 mmol) of tetrafluorophthalonitrile, 0.91 g (5 mmol) of tetrafluorohydroquinone and 20 ml of N,N-dimethylformamide (DMF). The flask containing the mixture was immersed in an ice-water bath to keep the mixture at 0 to 5° C. To the mixture was added dropwise in 10 minutes 1.01 g (10 mmol) of triethylamine, and the resulting mixture was stirred at that temperature for 20 minutes and then at room temperature for 30 minutes. The contents were poured into 0.2 liter of hydrochloric acid to precipitate an oily substance in a lower layer. After separation, the oily substance was washed with water and dried. Recrystallization of it from methanol afforded 1.12 g of a product in a yield of 63% as 1,4-bis(3,4-dicyanotrifluorophenoxy)tetrafluorobenzene.

Upon measurement of $^1$H-NMR spectrum in DMSO-$d_6$ using TMS as an internal standard, no signal was observed, which indicated absence of hydrogen atoms. As a result of $^{19}$F-NMR analysis in DMSO-$d_6$ using $CFCl_3$ as an internal standard, four signals were observed whose integral ratio was 4:2:2:2 from the upfield side.

In elemental analysis of the product, calculated values of carbon and nitrogen were 48.69% and 10.33%, respectively, while found values thereof were 48.83% and 10.21%, respectively, and well corresponded to the calculated values.

From the above results, the compound obtained as a result of this reaction was confirmed to be 1,4-bis(3,4-dicyanotrifluorophenoxy)tetrafluorobenzene, the objective compound.

Example 17

In an Erlenmeyer flask were charged 40.0 g (0.2 mol) of tetrafluorophthalonitrile and 0.1 liter of DMF. The flask containing the mixture was immersed in an ice-water bath to keep the mixture at 0 to 5° C. To the mixture was added portionwise in 10 minutes 11.3 g (0.05 mol) of disodium tetrafluorohydroquinone. The resulting mixture was stirred at that temperature for 20 minutes and then at room temperature for 30 minutes. Thereafter, the reaction mixture was treated in the same manner as in Example 16 and the product was identified in the same manner as in Example 16. Thus 14.6 g of 1,4-bis(3,4-dicyanotrifluorophenoxy) tetrafluorobenzene was obtained in a yield of 54%.

Example 18

In an eggplant type flask were charged 2.90 g (10 mmol) of 1,4-difluoropyromellitic acid and 10.2 g (0.2 mol) of acetic anhydride. The mixture was reacted under reflux for 2 hours. After completion of the reaction, the flask was left to stand to decrease the temperature of the contents down to room temperature. White solids which precipitated were filtered and dried to obtain 1.82 g of a product in a yield of 72% as 1,4-difluoropyromellitic dianhydride. Upon infrared absorption spectroscopy of the product, an absorption at 2,500 to 3,700 cm$^{-1}$ due to a hydroxyl group in carboxylic acid and an absorption at near 1,750 cm$^{-1}$ due to a carbonyl group observed on 1,4-difluoropyromellitic acid disappeared and instead absorptions at 1,850 cm$^{-1}$ and 1,800 cm$^{-1}$, respectively, specific to a carbonyl group of an acid anhydride appeared.

Upon measurement of $^1$H-NMR spectrum in DMSO-$d_6$ using TMS as an internal standard, no signal was observed, which indicated absence of hydrogen atoms. As a result of $^{19}$F-NMR analysis in DMSO-$d_6$ using $CFCl_3$ as an internal standard, a single line was observed at –118.7 ppm.

In elemental analysis of the product, calculated value of carbon was 47.27% while found value thereof was 47.38%, and well corresponded to the calculated values.

From the above results, the compound obtained as a result of this reaction was confirmed to be 1,4-difluoropyromellitic dianhydride, the objective compound.

Example 19

In an eggplant type flask were charged 2.14 g (10 mmol) of 1,4-difluorotetracyanobenzene and 10 ml of 80% sulfuric acid, and the mixture was stirred at 200° C. for 2 hours. After completion of the reaction, the flask was left to stand to decrease the temperature of the contents down to room temperature. White solids which precipitated were filtered and quickly washed with deionized water, followed by drying to obtain 1.89 g of a product in a yield of 74% as 1,4-difluoropyromellitic dianhydride. In the same manner as in Example 18, the product was confirmed to be 1,4-difluoropyromellitic dianhydride, the objective compound.

Example 20

In an eggplant type flask were charged 10.88 g (51 mmol) of 1,4-difluorotetracyanobenzene and 125 ml of 60% sulfuric acid. The mixture was reacted at 150° C. for 5 hours. After completion of the reaction, the flask was left to stand to decrease the temperature thereof down to room temperature. White solids which precipitated were filtered and washed with deionized water sufficiently. The solids were dried at 100° C. under vacuum to obtain 12.86 g of a white product in a yield of 87% as 1,4-difluoropyromellitic acid. Upon infrared absorption spectroscopy of the product, an absorption at 2,250 cm$^{-1}$ due to a cyano group observed on 1,4-difluorotetracyanobenzene disappeared and an absorption at 2,500 to 3,700 cm$^{-1}$ due to a hydroxyl group in a carboxylic acid and an absorption at near 1,750 cm$^{-1}$ due to a carbonyl group in a carboxylic acid appeared newly.

As a result of $^{19}$F-NMR analysis in DMSO-$d_6$ using $CFCl_3$ as an internal standard, a single line was observed at –119.3 ppm.

In elemental analysis of the product, calculated values of carbon and hydrogen were 36.11% and 1.52%, respectively, while found values thereof were 36.26% and 1.48%, respectively, and well corresponded to the calculated values.

From the above results, the compound obtained as a result of this reaction was confirmed to be 1,4-difluoropyromellitic acid, the objective compound.

TABLE 1

Type and amount of acid anhydride and of diamine as well as amount of solvent used in Examples 2 to 12

| Example | Acid Anhydride | | Diamine | | Solvent |
|---|---|---|---|---|---|
| 2 | 10FEDA | 11.64 g | 4FPPD | 3.60 g | 86 g |
| 3 | 10FEDA | 11.64 g | 8FODA | 6.88 g | 105 g |
| 4 | 10FEDA | 11.64 g | 8FSDA | 7.20 g | 107 g |
| 5 | P2FDA | 5.08 g | 4FMPD | 3.60 g | 49 g |
| 6 | P2FDA | 5.08 g | 4FPPD | 3.60 g | 49 g |
| 7 | P2FDA | 5.08 g | 8FODA | 6.88 g | 68 g |
| 8 | P2FDA | 5.08 g | 8FSDA | 7.20 g | 70 g |
| 9 | P6FDA | 7.08 g | 4FMPD | 3.60 g | 61 g |
| 10 | P6FDA | 7.08 g | 4FPPD | 3.60 g | 61 g |
| 11 | P6FDA | 7.08 g | 8FODA | 6.88 g | 79 g |
| 12 | P6FDA | 7.08 g | 8FSDA | 7.20 g | 81 g |

The invention has been described in detail with respect to various embodiments, and it will now be apparent from the foregoing to those skilled in the art that changes and modifications may be made without departing from the invention in its broader aspects, and it is the intention, therefore, in the appended claims to cover all such changes and modifications as far as fall within the true spirit of the invention.

What is claimed is:

1. A method for preparing 1,4-difluoropyromellitic dianhydride represented by formula (12):

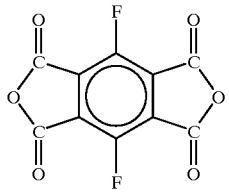

(12)

comprising:

dehydrating 1,4-difluoropyromellitic acid represented by formula (15):

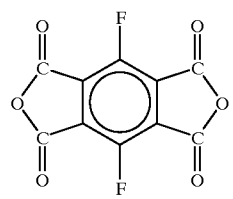

(15)

2. A method for preparing 1,4-difluoropyromellitic dianhydride represented by formula (12):

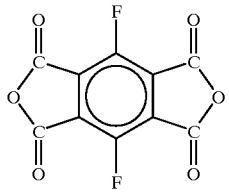

(12)

comprising:

hydrolyzing and dehydrating 1,4difluorotetracyanobenzene represented by formula (18):

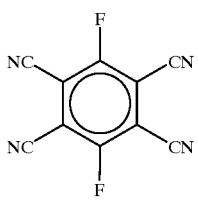

(18)

in sulfuric acid.

3. A method for preparing 1,4-difluoropyromellitic acid represented by formula (15)

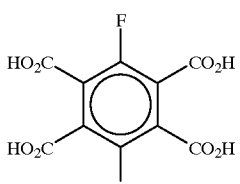

(15)

comprising:

hydrolyzing 1,4-difluorotetracyanobenzene represented by formula (18):

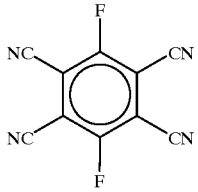

(18)

* * * * *